United States Patent
Kozhevnikov

(10) Patent No.: US 11,498,936 B2
(45) Date of Patent: Nov. 15, 2022

(54) PREPARATION OF METAL-PYRIDINE DERIVATIVE COMPLEXES FOR USE IN MEDICAL IMAGING

(71) Applicant: University of Northumbria at Newcastle, Newcastle upon Tyne (GB)

(72) Inventor: Valery Kozhevnikov, Newcastle upon Tyne (GB)

(73) Assignee: University of Northumbria at Newcastle, Newcastle upon Tyne (GB)

( * ) Notice: Subject to any disclaimer, the term of this patent is extended or adjusted under 35 U.S.C. 154(b) by 241 days.

(21) Appl. No.: 16/769,150

(22) PCT Filed: Dec. 13, 2018

(86) PCT No.: PCT/GB2018/053615
§ 371 (c)(1),
(2) Date: Jun. 2, 2020

(87) PCT Pub. No.: WO2019/116037
PCT Pub. Date: Jun. 20, 2019

(65) Prior Publication Data
US 2020/0369698 A1    Nov. 26, 2020

(30) Foreign Application Priority Data
Dec. 13, 2017  (GB) ..................................... 1720769

(51) Int. Cl.
*C07F 15/00* (2006.01)
*A61K 51/04* (2006.01)

(52) U.S. Cl.
CPC ...... *C07F 15/0033* (2013.01); *A61K 51/0472* (2013.01); *C07F 15/0086* (2013.01)

(58) Field of Classification Search
None
See application file for complete search history.

(56) References Cited

U.S. PATENT DOCUMENTS

2013/0189184 A1   7/2013   Lub et al.

FOREIGN PATENT DOCUMENTS

WO   2010/051530 A2   5/2010

OTHER PUBLICATIONS

Hajbi et al. General synthetic approach to 4-substituted 2,3-dihydrofuro[2,3-b]pyridines and 5-substituted 3,4dihydro2H-pyrano[2,3-b]pyridines. 2009 Synlett 1: 92-96. (Year: 2009).*
International Search Report and Written Opinion issued in counterpart PCT Application No. PCT/GB2018/053615 dated Feb. 21, 2019 (fifteen (15) pages).
Li, Steve Po Yam et al. 2016. "Installing an additional emission quenching pathway in the design of iridium (III)-based phosphorogenic biomaterials for bioorthogonal labelling and imaging." Biomaterials. vol. 103, pp. 305-313.
Horner, Katherine A. et al. 2015. "Strain-promoted reaction of 1,2,4-Triazines with Bicyclononynes." Chemistry—A European Journal. vol. 21, No. 41, pp. 14376-14381.
Great Britain Search Report issued in counterpart GB Application No. 1720769.7 dated Aug. 17, 2018 (four (4) pages).
Zvirzdinaite, M. et al. 2017. "Palladium(II) Complexes of Ambidentate and Potentially Cyclometalating 5-Aryl-2-(2'-pyridyl)-1,2,4-triazine Ligands." European Journal of Inorganic Chemistry. vol. 2017, No. 13, pp. 2011-2022.
Kamber, D. et al. 2015. "1,2,4-Triazines Are Versatile Bioorthogonal Reagents." Journal of the American Chemical Society. vol. 134, No. 26, pp. 8388-8391.
Berthonneau, C. et al. 2017. "Organocatalyzed Thia-Michael Addition and Sequential Inverse Electron Demanding Diels-Alder Reaction to 3-Vinyl-1,2,4-triazine Platforms." Advanced Synthesis & Catalysis. vol. 359, No. 23, pp. 4106-4110.
Pipkom, R. et al. 2009. "Inverse-electron-demand Diels-Alder reaction as a highly efficient chemoselective ligation procedure: Synthesis and function of a Bioshuttle for temozolomide transport into prostate cancer cells." Journal of Peptide Science. vol. 15, No. 3, pp. 235-241.

* cited by examiner

*Primary Examiner* — Jennifer Lamberski
(74) *Attorney, Agent, or Firm* — Nexsen Pruet, PLLC; E. Eric Mills; Nicholas P. Stadnyk

(57) ABSTRACT

The present invention relates to methods of forming metal-pyridine derivative complexes using pericyclic reactions with metal-1,2,4-triazine derivative complexes and a dienophile as the reactants. The reactants are bioorthogonal and the methods are particularly useful in preparing imaging agents.

28 Claims, No Drawings

PREPARATION OF METAL-PYRIDINE DERIVATIVE COMPLEXES FOR USE IN MEDICAL IMAGING

CROSS REFERENCE TO RELATED APPLICATIONS

This application is a 35 U.S.C. § 371 U.S. national phase entry of International Application No. PCT/GB2018/053615 having an international filing date of Dec. 13, 2018, which claims the benefit of Great Britain Application No. 1720769.7 filed Dec. 13, 2017, each of which is incorporated herein by reference in its entirety.

The invention relates to methods of forming pyridines using pericyclic reactions. The methods involve reacting a triazine that is complexed to a metal with a dienophile. The reactants are bioorthogonal and the methods are particularly useful in medical imaging and in delivering therapeutic agents to particular tissue or site. The invention also relates to kits for carrying out said methods.

BACKGROUND TO THE INVENTION

In many areas of medicine, it is desirable to target a drug or diagnostic agent to a specific tissue or site. In particular in medical imaging the delivery of imaging agents to a particular tissue is crucial. Successful imaging requires that the imaging agent has high target uptake but that excess agent is rapidly cleared from the non-targeted tissues. Typically the targeting step is time consuming and this can lead to excessive exposure of the body to the imaging agent, which can often be harmful (e.g. radionucleotides). However, this is a balance that is difficult to achieve and as a result so-called pretargeting methods have been developed.

Pretargeting involves the targeting of the desired primary target (e.g. the tissue to be imaged) with a first probe having both a moiety that has high affinity for the primary target and a secondary target moiety. Once the primary targeting step is complete, typically a time-consuming process, a second probe, having both a moiety that has high affinity for the secondary target and the imaging moiety is administered. The secondary target moiety and the moiety having high affinity for the target moiety react, resulting in the imaging or therapeutic moiety being attached to the primary target.

Initial pretargeting was carried out using secondary coupling pairs that were natural in origin (e.g. antibody-antigen or biotin-streptavidin) but these methods had their own problems such as break down of the secondary pair via natural decomposition pathways.

An alternative methodology is the use of a bioorthogonal secondary coupling pair, i.e. using two chemical functionalities that have a high reactivity with each other but a low reactivity with biological systems. In this way, bioorthogonal reactions can be carried out in living systems without interfering with intracellular processes.

Bioorthogonal chemistry is emerging as a powerful tool to visualize proteins, nucleic acids, glycans and other biomolecules. (M. Boyce, C. R. Bertozzi, Nat Meth 2011, 8, 638-642; K. Lang, J. W. Chin, ACS Chemical Biology 2014, 9, 16-20.) Bioorthogonal reactions are based on reagents that selectively react with each other but do not react with any of the naturally present molecules. Bioorthogonal reactions should be kinetically fast under physiological conditions and should not interfere with any natural biochemical processes. The reagents and the side products should be non-toxic. (T. Carell, M. Vrabel, Topics in Current Chemistry 2016, 374, 1-21.)

One problem with such approaches is that the reaction between the bioorthogonal groups is still quite slow. In the cellular environment, the concentrations of proteins or other biomolecules is very low and the bioorthogonal reactions should be very fast. For in vivo applications, the rate constant should be 1 $M^{-1}s^{-1}$ or higher A further problem is that the second probe, comprising the imaging agent, still needs to be cleared from the non-targeted tissues before the imaging of the targeted tissues can be carried out, making such imaging processes time consuming.

One common example of bioorthogonal reaction is the inverse electron demand Diels Alder (IED-DA) reaction of electron deficient 1,2,4,5-tetrazines with strained alkenes and alkynes (see WO2010/051530; US2013/0189184; Biomaterials 2016, 103, 305-313; Chemical Society Reviews 2017, 46, 4895-4950). The reactions are fast, do not require catalysts and produce non-toxic dinitrogen as the only by-product. However, tetrazine derivatives can be unstable and degrade under physiological conditions.

To address this problem, very recently 1,2,4-triazines were developed as IED-DA bioorthogonal reagents offering better stability under physiological conditions. For example, the Prescher and later Vrabel groups studied the reaction of 1,2,4-triazines with derivatives of trans-cyclooctyne-ols (TCO) reporting second order rate constant in the range of $k_2=1$-$7.5\times10^{-2}$ $M^{-1}s^{-1}$. (J. Am. Chem. Soc. 2015, 137, 8388-8391). The use of the most reactive trans-bicyclononene (s-TCO) increases the reaction rate with the highest reported values of $k_2=25$ $M^{-1}s^{-1}$. There is very little literature data about the kinetics of the reaction of 1,2,4-triazines with strained alkynes. Webb group investigated the reaction of 3-substituted-1,2,4-triazine with (1R,8S,9R)-bicyclo[6.1.0]non-4-yn-9-ylmethanol (BCN) reporting the rate constant of $k_2=3$-$5\times10^{-4}$ $M^{-1}s^{-1}$ (K. A. Homer, N. M. Valette, M. E. Webb, Chemistry—A European Journal 2015, 21, 14376-14381). Unfortunately, none of the 1,2,4-triazine derivatives developed to date satisfy this criteria.

In a more general context, pyridines are common motifs found in pharmaceuticals, agrochemicals, functional materials, catalytic ligands and new, more efficient ways of making them are inherently desirable.

STATEMENT OF THE INVENTION

In a first aspect of the invention is provided a method of forming a pyridine; the method comprising:
   contacting a 1,2,4-triazine with a dienophile to form a pyridine;
   wherein the 1,2,4-triazine starting material is complexed to a metal.

The triazine may be complexed to the metal through any of its nitrogen atoms.

It may be that both the 1,2,4-triazine starting material and the pyridine product material are complexed to the metal. This will typically be the case where the 1,2,4-triazine is complexed to the metal through the nitrogen at the 4 position.

The inventors have found that the rate of reaction of an inverse electron demand Diels-Alder/retro-Diels-Alder (IEDDA/RDA) reaction is very significantly increased by complexing the 1,2,4-triazine with a metal. This effect is observed irrespective of which nitrogen of the 1,2,4-triazine the metal is complexed to.

In particular, these reactions can prove useful in the context of the imaging of biological samples using a bioorthogonal pretargeting method.

Thus, in a second aspect of the invention is provided a kit for medical imaging or for imaging a biological sample, the kit comprising:

a 1,2,4-triazine; and a dienophile;

wherein the 1,2,4-triazine is complexed to a metal; and wherein either:

A) the 1,2,4-triazine is attached to a biological targeting moiety; or

B) the dienophile is attached to a biological targeting moiety.

In addition to the increased rate of reaction relative to the prior art bioorthogonal pretargeting methods, the present invention provides further benefits. The inventors have found that metals that are useful for medical imaging can accelerate the IEDDA/RDA. This means that the metal that is complexed to the product pyridine can itself be the imaging agent, simplifying the structure of the relevant probe. Furthermore, metal complexed triazine compounds tend to be more soluble in aqueous media than the equivalent uncomplexed triazine compounds and more stable in physiological media than similar tetrazines. This is expected to simplify the formulation and medical administration of the probes comprising the triazine and/or remove the need to add functionality to the probes to get the desired solubility characteristics.

The metal complexes can also be more photostable than conventional organic luminophores. Metal complexes can also possess long-lived luminescence and therefore provide an opportunity for time-resolved techniques to eliminate background luminescence.

In a further particular benefit, certain pyridine metal complexes formed in the methods of the invention, such as complexes of Ir(III), Ru(II) or Re(I), fluoresce when complexed to the product pyridine but do not fluoresce when complexed to the starting triazine. The luminogenic probes that "switch on" after binding to the target are particularly useful because the luminescent background of non-conjugated imaging agent is not present. This eliminates the need to wait while the imaging agent clears from the system.

Another benefit of this strategy is that the metal centre brings additional functionality, such as luminescent properties that are superior to organic fluorophores. For example, cyclometallated iridium (III) and Pt(II) complexes are among the brightest emitters used in bioimaging and bioorthogonal chemistry. They are photostable and their photophysical properties can be tuned and long-lived emission provides opportunity for time-delayed elimination of back-ground luminescence. Metal complexes are also used in traditional, photodynamic and radio therapies, in nuclear imaging and as MRI contrast agents.

Triazines

The 1,2,4-triazine will typically form part of a larger compound. It may be that the compound comprising the 1,2,4-triazine is a compound of formula (I):

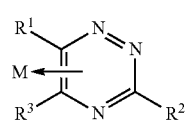

(I)

wherein M is the metal, which may be bonded to other ligands;

$R^1$, $R^2$ and $R^3$ are each independently selected from H, $C_1$-$C_6$-alkyl, $C_1$-$C_6$-haloalkyl, $C_3$-$C_6$ alkenyl, $C_1$-$C_6$-alkynyl, halo, nitro, cyano, $C(O)R_4$, $(CH_2)_nCO_2R^4$, $OR^4$, $SR^4$, $NR^4R^5$, $C(O)NR^4R^4$, $S(O)R^4$, $S(O)_2R^4$, $C_3$-$C_6$-cycloalkyl, 3-18-membered heterocycloalkyl, 5-, 6-, 9-, 10- or 14-membered heteroaryl, phenyl, naphthyl, pyrenyl and fluorophore; or $R^1$ and $R^3$, together with the atom to which they are attached, form a monocyclic or polycyclic aryl or heteroaryl;

wherein if any of $R^1$, $R^2$ and $R^3$ are $C_1$-$C_6$-alkyl, $C_3$-$C_6$-cycloalkyl, 3-6-membered heterocycloalkyl, 5-, 6-, 9-, 10- or 14-membered heteroaryl, phenyl, naphthyl or pyrenyl that group can be substituted with from 1 to 5 $R^6$ groups;

$R^4$ is independently at each occurrence selected from H and $C_1$-$C_4$-alkyl; and $R^5$ is independently at each occurrence selected from H, $C_1$-$C_4$-alkyl, $C(O)$—$C_1$-$C_4$-alkyl and $S(O)_2$—$C_1$-$C_4$-alkyl;

$R^6$ is selected from 3-18-membered heterocycloalkyl, 5-, 6-, 9-, 10- or 14-membered heteroaryl, fluorophore, phenyl, naphthyl, $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $N((CH_2)_nCO_2R_4)_2$, $C(O)NR^4R^4$, $S(O)R^4$ and $S(O)_2R^4$;

wherein if $R^6$ is 3-18-membered heterocycloalkyl, $C_1$-$C_6$-alkyl, 5-, 6-, 9-, 10- or 14-membered heteroaryl, phenyl, or naphthyl, $R^6$ can be substituted with from 1 to 5 $R^7$ groups;

$R^7$ is selected from 3-18-membered heterocycloalkyl, 5-, 6-, 9-, 10- or 14-membered heteroaryl, fluorophore, phenyl, naphthyl, $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $N((CH_2)_nCO_2R_4)_2$, $C(O)NR^4R^4$, $S(O)R^4$ and $S(O)_2R^4$;

wherein if $R^7$ is 3-18-membered heterocycloalkyl, $C_1$-$C_6$-alkyl, 5-, 6-, 9-, 10- or 14-membered heteroaryl, phenyl, or naphthyl then $R^7$ can be substituted with from 1 to 5 $R^8$ groups;

$R^8$ is selected from $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $C(O)NR^4R^4$, $S(O)R^4$ and $S(O)_2R_4$;

wherein the 1,2,4-triazine is optionally attached to a biological targeting moiety via one of the alkyl, $C_3$-$C_6$-alkenyl, $C_1$-$C_6$-alkynyl, $C_3$-$C_6$-cycloalkyl, 3-6-membered heterocycloalkyl, 5-, 6-, 9- 10- or 14-membered heteroaryl, phenyl, naphthyl groups mentioned above;

n is independently at each occurrence an integer selected from 0, 1 and 2;

where any of $R^6$, $R^7$ or $R^8$ are phenyl, said phenyl group may be bonded to the metal;

where any of $R^2$, $R^3$, $R^6$, $R^7$ or $R^8$ are $SR^4$, $NR^4R^5$, $(CH_2)_nCOOR^4$, $OR^4$ or $N((CH_2)_nCO_2R_4)_2$, $R^4$ may be absent and the heteroatom (S, N or O) may be bonded to the metal.

Typically the compound comprising the triazine will be either bonded or complexed to the metal via more than one position, e.g. via more than 1 atom.

Any trivalent nitrogen atom may, for example, complex to the metal, (e.g. a nitrogen of a group selected from tertiary amine, pyridine, pyrazole, triazine, etc). For the absence of doubt, the triazine may be complexed to M via any one of the nitrogen atoms in the triazine ring.

For the absence of doubt, 'other ligands' means ligands other than the compound comprising the triazine.

In an embodiment, the compound of formula (I) is a compound of formula (Ia):

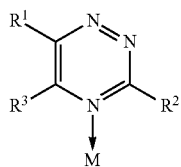

wherein M, $R^1$, $R^2$ and $R^3$ are as described above for compounds of formula (I).

In an embodiment, the compound of formula (I) is a compound of formula (Ib):

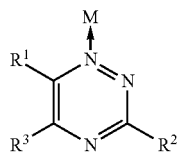

wherein M, $R^1$, $R^2$ and $R^3$ are as described above for compounds of formula (I).

In an embodiment, the compound of formula (I) is a compound of formula (Ic):

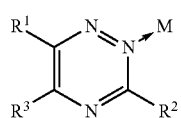

wherein M, $R^1$, $R^2$ and $R^3$ are as described above for compounds of formula (I).

The following embodiments apply to compounds of any of formulae (I) and (Ia)-(Ic). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

It may be that $R^2$ is a 5-, 6-, 9-, 10- or 14-membered heteroaryl group. It may be that $R^2$ is a 2-pyridyl group. It may be that $R^2$ is a phenyl group. It may be that $R^2$ is a phenyl group that is bonded to the metal at a position next to the point of attachment of $R^2$ to the triazine. Said phenyl group may itself be substituted at a position next to the carbon which is bonded to the metal by a 5-, 6-, 9-, 10- or 14-membered heteroaryl group, e.g. a 2-pyridyl group. Said pyridyl group may be substituted, next to the nitrogen atom, by a phenol group that is bonded to the metal.

It may be that $R^3$ is a 5-, 6-, 9-, 10- or 14-membered heteroaryl group. It may be that $R^3$ is a 2-pyridyl group. It may be that $R^3$ is a 1-pyrazolyl group. It may be that $R^3$ is a pyrenyl group. It may be that $R^3$ is a 1-pyrenyl group. It may be that $R^3$ is a phenyl group. It may be that $R^3$ is a phenyl group that is bonded to the metal at a position next to the point of attachment of $R^3$ to the or triazine. Said phenyl group may itself be substituted at a position next to the carbon which is bonded to the metal by a 5-, 6-, 9-, 10- or 14-membered heteroaryl group, e.g. a 2-pyridyl group. Said pyridyl group may be substituted, next to the nitrogen atom, by a phenol group that is bonded to the metal. In these embodiments, $R^2$ may be H.

It may be that $R^1$ is H. It may be that $R^1$ is $C_1$-$C_4$-alkyl.

It may be that $R^1$ and $R^3$, together with the atom to which they are attached, form a monocyclic or polycyclic aryl or heteroaryl. It may that $R^1$ and $R^3$, together with the atom to which they are attached forms

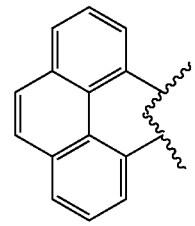

It may be that $R^6$ is a 5-, 6-, 9-, 10- or 14-membered heteroaryl group. It may be that $R^6$ is a 2-pyridyl group. It may be that $R^6$ is $C_1$-$C_6$-alkyl. It may be that $R^6$ is $C_1$-alkyl. It may be that $R^6$ is a 3-18-membered heterocycloalkyl. It may be that $R^6$ is a 12-membered heterocycloalkyl. It may be that $R^6$ is

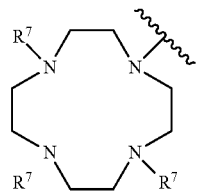

It may be that when $R^6$ is

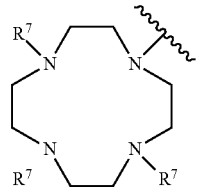

$R^7$ is $(CH_2)_n COOR^4$ and $R^4$ is absent and the oxygen is bonded to the metal. It may be that when $R^6$ is

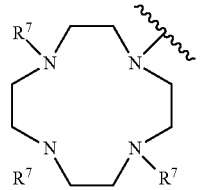

$R^7$ may be $(CH_2)_n COOR^4$, wherein n=1 and $R^4$ is absent and the oxygen is bonded to the metal. In these embodiments, $R^6$ may be comprised in $R^2$ or $R^3$. In these embodiments, $R^2$ or $R^3$ may be $C_1$-$C_6$-alkyl substituted with $R^6$. In these embodiments, $R^2$ or $R^3$ may be $C_1$-alkyl substituted with $R^6$.

It may be that $R^6$ is a fluorophore.

It may be that $R^7$ is a 3-18-membered heterocycloalkyl. It may be that $R^7$ is a 12-membered heterocycloalkyl. It may be that $R^7$ is

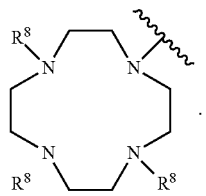

It may be that when $R^7$ is

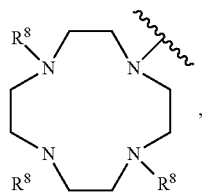

$R^8$ is $(CH_2)_n COOR^4$ and $R^4$ is absent and the oxygen is bonded to the metal. It may be that when $R^7$ is

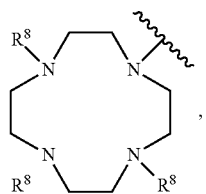

$R^8$ is $(CH_2)_n COOR^4$, wherein n=1 and $R^4$ is absent and the oxygen is bonded to the metal. In these embodiments, $R^7$ may be comprised in $R^6$. In these embodiments, $R^6$ may be $C_1$-$C_6$-alkyl substituted with $R^7$. In these embodiments, $R^6$ may be $C_1$-alkyl substituted with $R^7$. In these embodiments, $R^6$ is typically comprised in an $R^2$ or $R^3$ group. Said $R^2$ or $R^3$ group may be pyridine, e.g. 2-pyridyl.

It may be that $R^7$ is a fluorophore.

It may be that the compound comprising the triazine has more than one position that is bonded to the metal. Thus, it may be that the compound comprising the triazine is bidentate, tridentate, tetradentate or polydentate. Bidentate, tridentate, tetradentate or polydentate triazines will typically comprise substituent groups that bond to the metal. Said bonding may include hydrogen bonding, dative bonding and covalent bonding.

It may be that $R^1$, $R^2$, $R^3$, $R^6$ and $R^7$ are selected such that the compound comprising the triazine may comprise a fluorophore, e.g. a single fluorophore. In other embodiments, the compound comprising the triazine may not comprise a fluorophore. It may be that triazene forms part of a fluorophore. For example, it may be that $R^1$ and $R^3$, together with the atom to which they are attached, form a monocyclic or polycyclic aryl or heteroaryl, which, along with the triazene ring, acts as a fluorophore.

The term 'fluorophore' refers to any group or compound that emits fluorescence. Typically, fluorophores will be bi-, tri- or poly-cyclic aromatic ring systems, or conjugated planar or cyclic system, that may comprise 1-4 heteroatoms independently selected from O, N, B or Si. Fluorophores may be derived from common fluorophores, such as coumarin, fluorescein, rhodamine and BODIPY.

Illustrative fluorophores include;

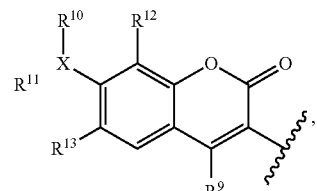

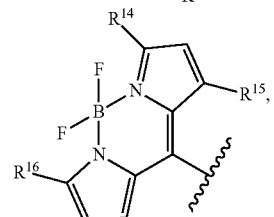

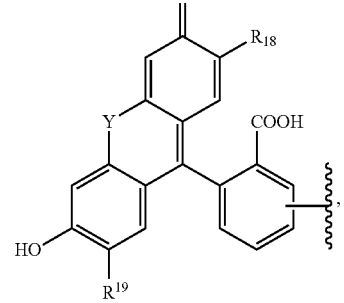

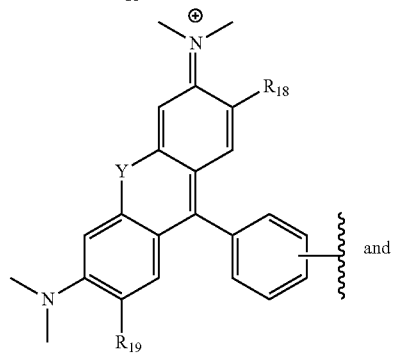

and

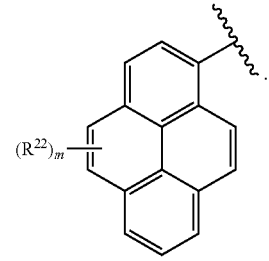

wherein $R^9$ is selected from H and Me;
X is selected from O and N;

$R^{10}$, $R^{11}$, $R^{12}$ and $R^{13}$ are each independently at each occurrence selected from halo, $C_1$-$C_6$-alkyl and H; or $R^{10}$ and $R^{12}$ together with the atom to which they are attached may form a 6-membered heterocycloalkyl group; and/or $R^{11}$ and $R^{13}$ together with the atom to which they are attached may form a 6-membered heterocycloalkyl group;

wherein if X is O, one of $R^{10}$ or $R^{11}$ is absent;

$R^{14}$, $R^{15}$, $R^{16}$ and $R^{17}$ are each independently at each occurrence selected from $C_1$-$C_6$-alkyl and H;

$R^{18}$ and $R^{19}$ are each independently at each occurrence selected from H or halo;

Y is O or $SiR^{20}R^{21}$;

$R^{20}$ and $R^{21}$ are each independently at each occurrence selected from H or $C_1$-$C_6$-alkyl;

wherein m is an integer between 1 and 9; and $R^{22}$ is independently at each occurrence selected from H, $C_1$-$C_6$-alkyl, $C_1$-$C_6$-haloalkyl, $C_3$-$C_6$ alkenyl, $C_1$-$C_6$-alkynyl, halo, nitro, cyano, $C(O)R_4$, $(CH_2)_nCO_2R^4$, $OR^4$, $SR^4$, $NR^4R^5$, $C(O)NR^4R^4$, $S(O)R^4$, $S(O)_2R^4$, $C_3$-$C_6$-cycloalkyl and phenyl.

More specifically, illustrative fluorophores include:

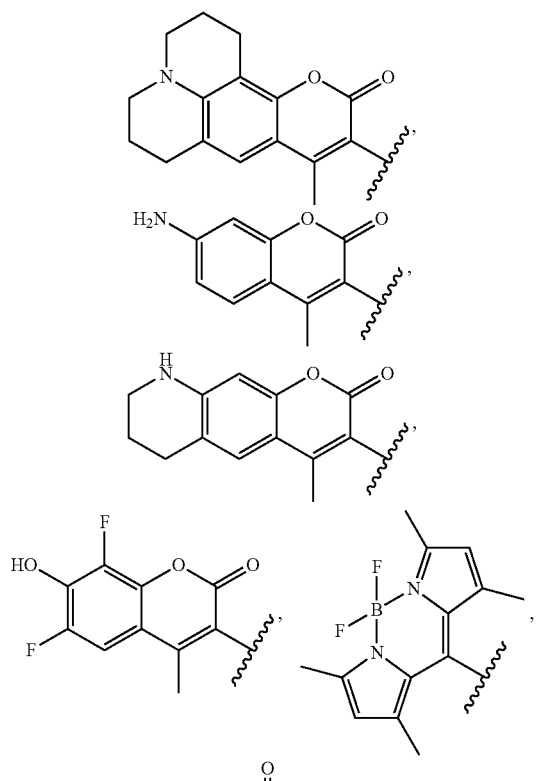

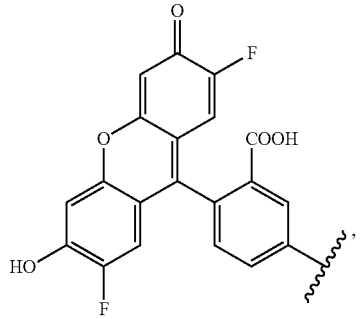

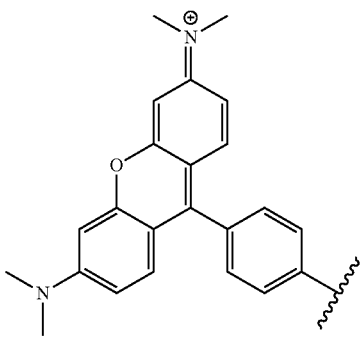

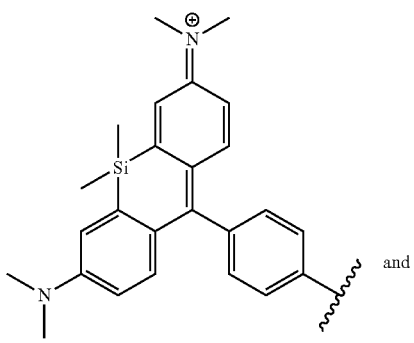

and

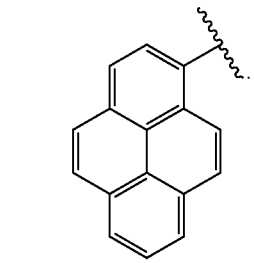

By way of illustration, compounds of formula (I) include:

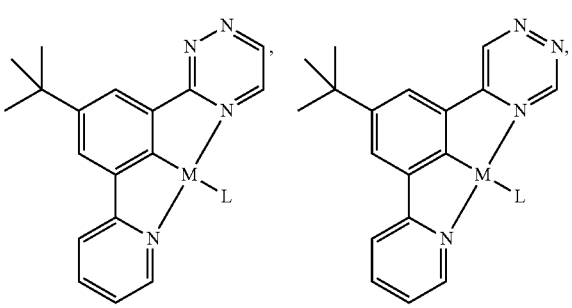

11
-continued
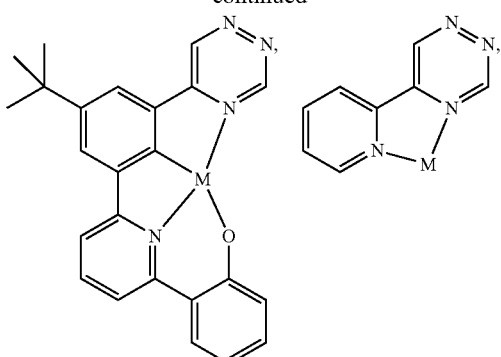
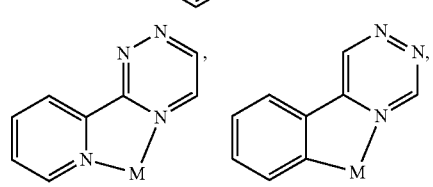
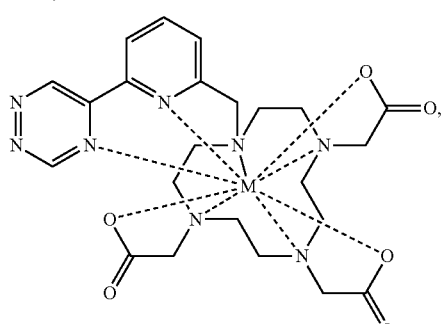
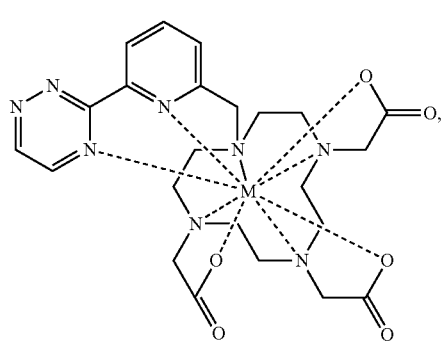
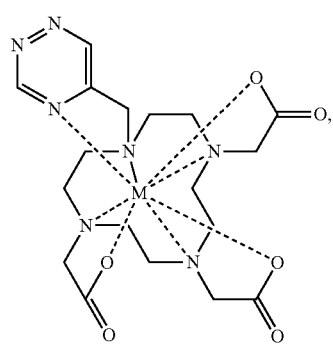
12
-continued
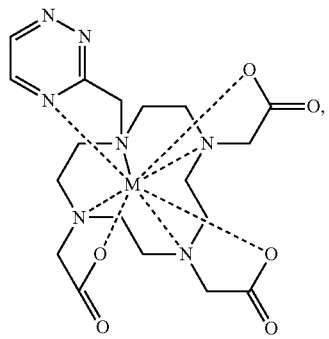
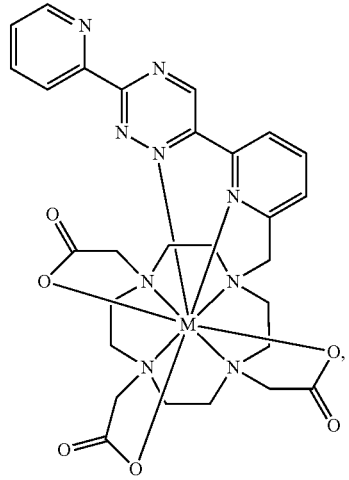
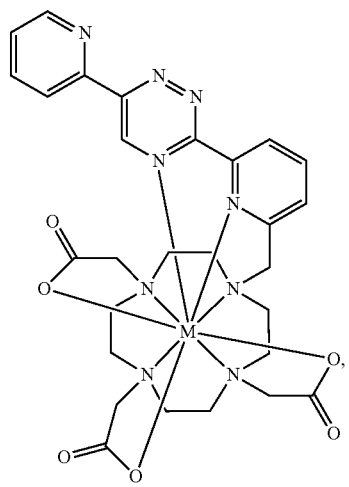

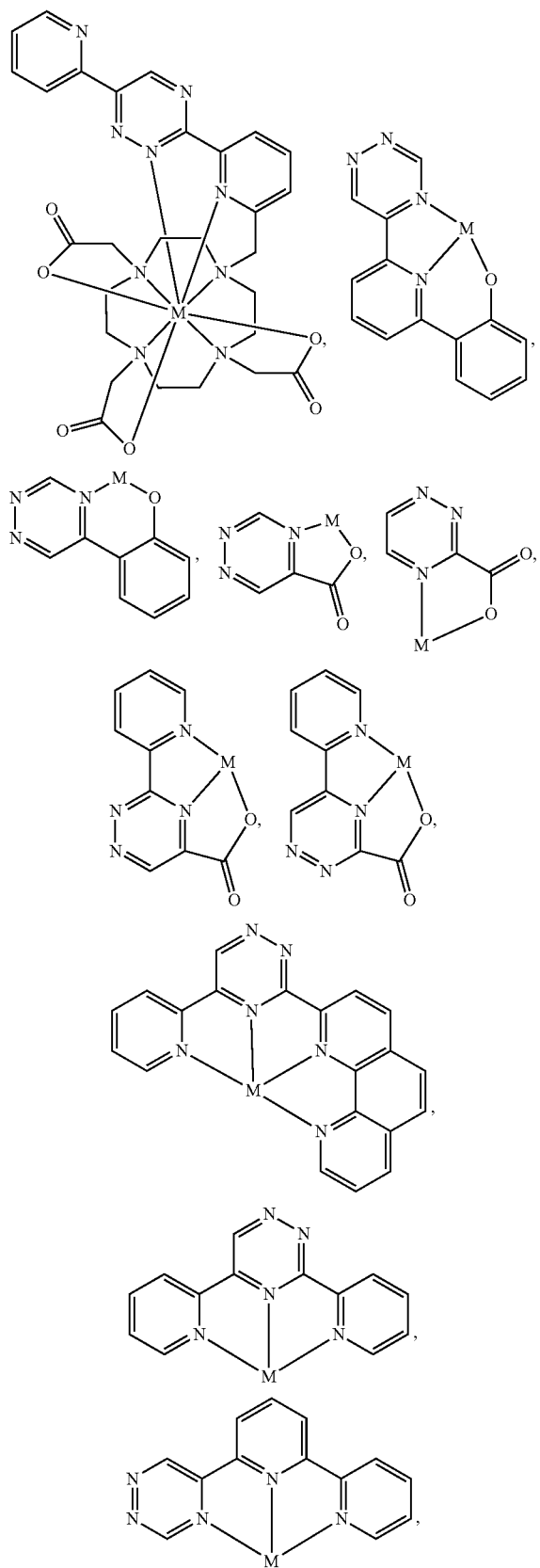
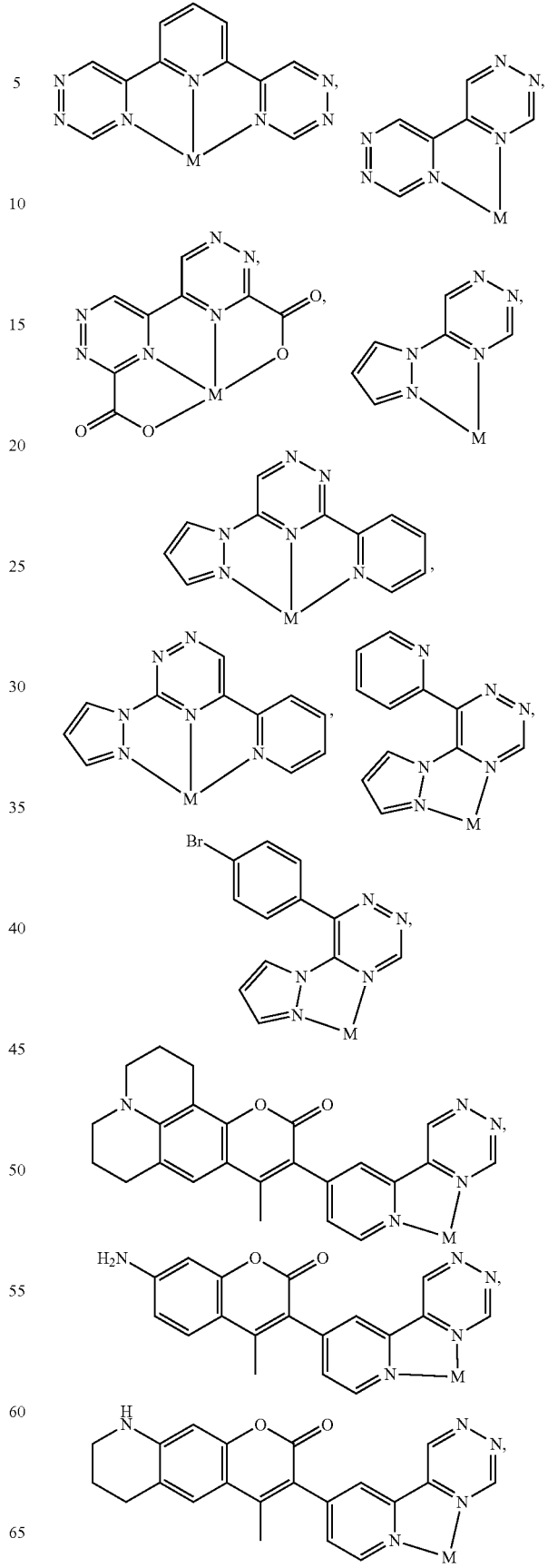

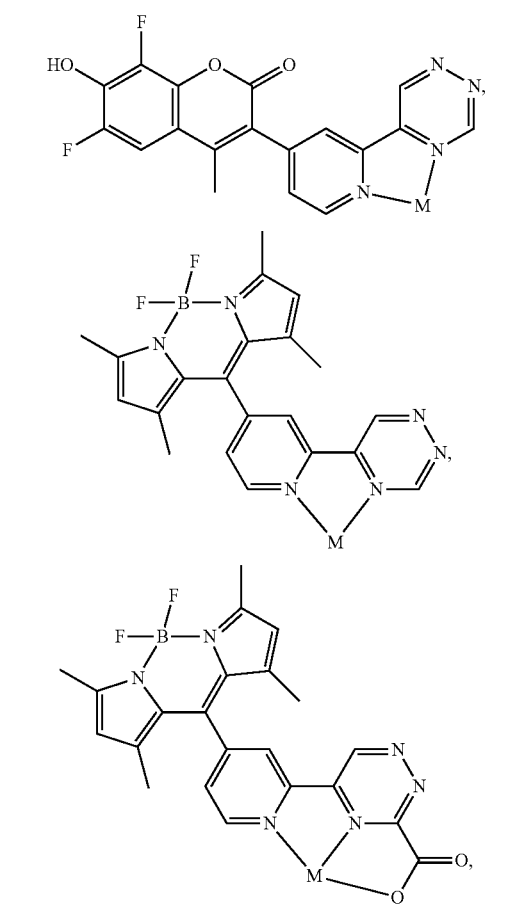
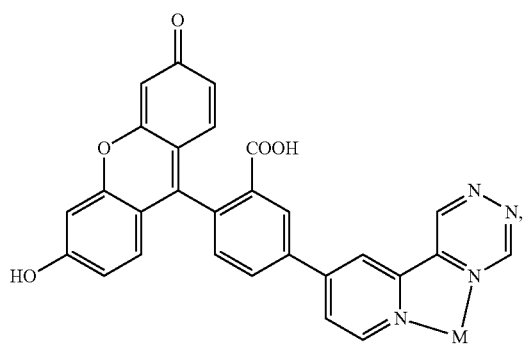
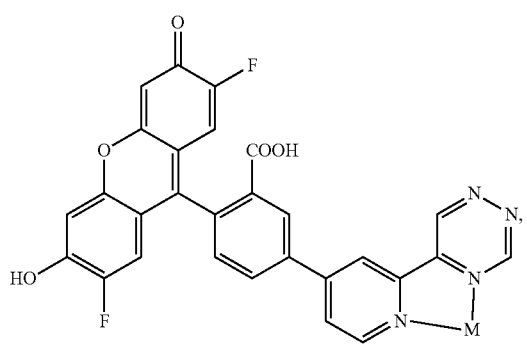
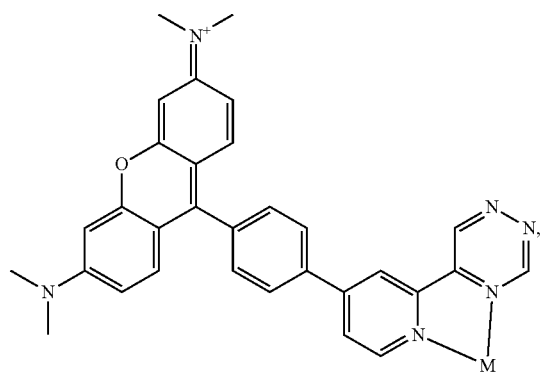
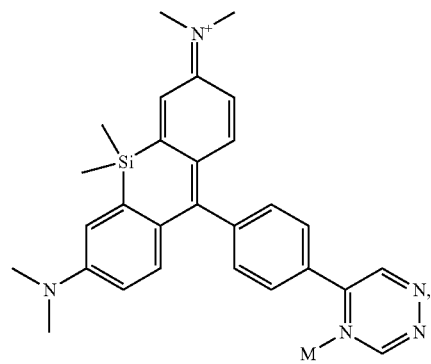

-continued

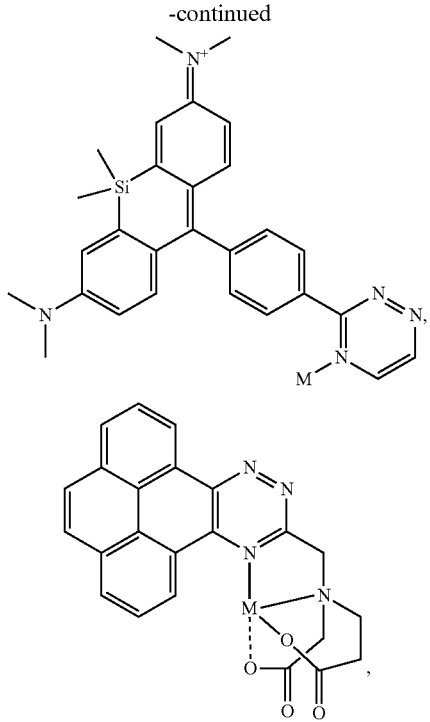

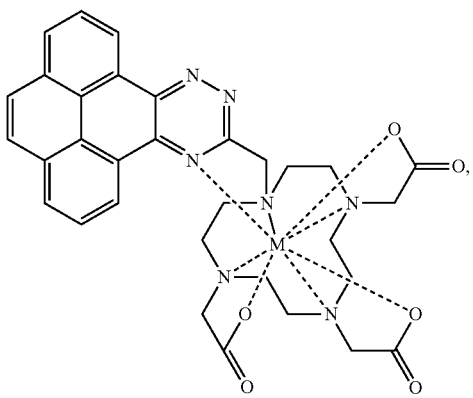

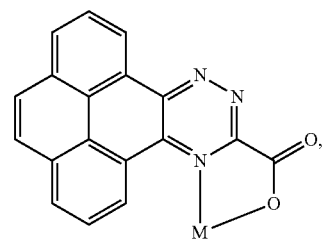

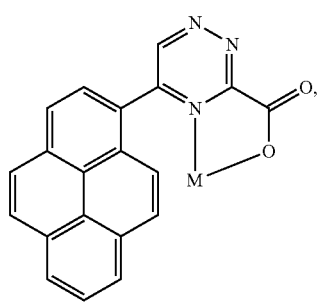

-continued

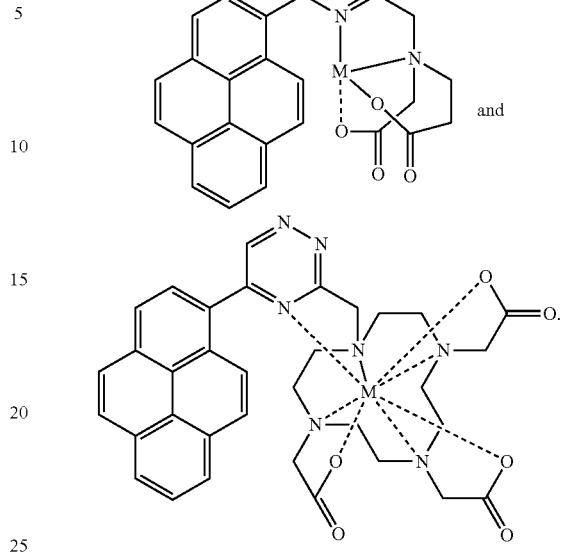

It may be that the 1,2,4-triazine is attached to a biological targeting moiety.

Dienophiles

The dienophile will be suitable for reacting in an inverse electron demand Diels Alder reaction. Thus, the dienophile will typically be electron rich.

The dienophile may be an enamine or a vinyl ether.

The dienophile may be an alkene or an alkyne. Where the dienophile is an alkene, it may be a monosubstituted alkene but will more typically be substituted with 2 or more groups. The dienophile may be a 1,2-disubstituted alkene. Where the alkene is 1,2-disubstituted it may be an E alkene or a Z alkene.

The dienophile may be a $C_3$-$C_{10}$-cycloalkene or $C_7$-$C_{10}$-cycloalkyne. The dienophile may be a $C_5$-$C_{10}$-cycloalkene. The dienophile may be a $C_7$-$C_{10}$-cycloalkene. The dienophile may be a cyclooctene or a cyclooctyne. The alkene of the cycloalkene (e.g. cyclooctene) may be an E alkene. The cycloalkene or cycloalkyne (e.g. cyclooctene or cyclooctyne) may be substituted with 1 to 5 substituent groups selected from $C_1$-$C_6$-alkyl, $C_1$-$C_6$-haloalkyl, halo, nitro, cyano, $C(O)R^{23}$, $CO_2R^{23}$, $OR^{23}$, $SR^{23}$, $NR^{23}R^{23}$, $CH_2OR^{23}$, $C(O)NR^{23}R^{23}$ and/or it may form a bicycle with a $C_3$-$C_6$-cycloalkane ring that is itself optionally substituted with from 1 to 3 groups selected from $C_1$-$C_6$-alkyl, $C_1$-$C_6$-haloalkyl, halo, nitro, cyano, $C(O)R^{23}$, $CO_2R^{23}$, $OR^{23}$, $SR^{23}$, $NR^{23}R^{23}$, $CH_2OR^{23}$, $C(O)NR^{23}R^{23}$; wherein $R^{23}$ is independently at each occurrence selected from H and $C_1$-$C_4$-alkyl. Where the dienophile is a cycloalkene, said substituent groups will typically not be attached to one of the alkene carbons.

The dienophile may be a dienophile as described in WO2010/051530 or US2013/0189184.

Metal

The following embodiments describe the metal that is complexed with the triazine. Thus, the following embodiments can be applied to M from formula (I), (Ia), (Ib) or (Ic):

The metal to which the triazine is complexed may be an uncharged metal atom or it may be a metal ion.

The metal may be a transition metal. The metal may be an actinide or a lanthanide.

The metal may be selected from Ru, Ir, Eu, Gd, Tb, Pt, Re and Zn. These metals provide luminogenic probes for luminescence imaging. The metal may be selected from radioactive isotopes of Tc and Ga. These metals provide probes for radiolabelling.

The metal may be complexed to more than one triazine, e.g. more than one triazine as depicted in formula (I).

The metal may be complexed to one or more ligands other than the compound comprising the triazine.

Said ligands may be anions, e.g. chloride, fluoride, bromide, carboxylates (e.g. acetate), alkoxides (e.g. methoxy, ethoxy).

Said ligands may form dative bonds with the metal. Thus, the ligands may be carbonyls, phosphines, amines or nitrogen containing heteroaryl compounds.

Said ligands may form organometallic bonds with the metal, e.g. phenyl groups.

Said ligands may be monodentate or said ligands may be bidentate, tridentate or polydentate.

Illustrative bidentate ligands include:

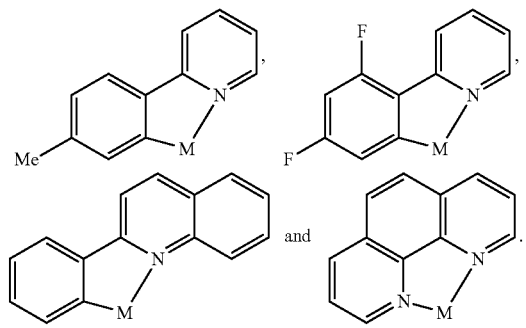

Biological Targeting Moiety

The biological targeting moiety is a moiety that is capable of binding to the biological target of interest.

These are typically biopolymeric molecules that have affinity for cell surface targets (e.g., membrane receptors), structural proteins (e.g., amyloid plaques), or intracellular targets (e.g., RNA, DNA, enzymes, cell signaling pathways). The biological targeting moiety may be selected from: a protein (including receptor binding proteins, antibodies and fragments of antibodies), an aptamer, an oligopeptide, an oligonucleotide, an oligosaccharide and a small organic molecule with recognised affinity with the desired receptor.

The biological targeting moiety preferably binds with high specificity and a high affinity, and the association with the biological target is preferably stable within biological conditions, e.g. in the body or in a cell.

Illustrative examples of biological targeting moieties include antibodies, antibody fragments, e.g. Fab2, Fab, scFV, diabodies, polymers proteins, peptides, e.g. octreotide and derivatives, VIP, MSH, LHRH, chemotactic peptides, bombesin, elastin, peptide mimetics, carbohydrates, monosaccharides, polysaccharides, viruses, whole cells, phage, drugs, chemotherapeutic agents, receptor agonists and antagonists, cytokines, hormones, steroids. Examples of organic compounds include: estrogens, e.g. estradiol, androgens, progestins, corticosteroids, paclitaxel, etoposide, doxorubricin, methotrexate, folic acid, and cholesterol. Further examples of protein biological targeting moieties of protein nature include interferons, e.g. alpha, beta, and gamma interferon, interleukins, and protein growth factor, such as tumor growth factor, e.g. alpha, beta tumor growth factor, platelet-derived growth factor (PDGF), uPAR targeting protein, apolipoprotein, LDL, annexin V, endostatin, and angiostatin. Examples of oligonucleotide biological targeting moieties include DNA, RNA, PNA and LNA which are complementary to the desired biological target.

The biological targeting moiety is attached to the triazine or to the dienophile. It may be attached via a covalent bond or via a linker group. The linker group may comprise from 1 to 500 atoms selected from O, C, N, S, P and H. The linker group may be a saturated or unsaturated alkylene chain, an aromatic or heteroaromatic group, a polyethylene glycol chain, or a fragment of a biopolymer, e.g. a peptide or oligonucleotide.

Inverse Electron Demand Diels-Alder/Retro Diels-Alder Reaction

The IEDDA/RDA reaction is illustrated in Scheme A (for alkynes) and Scheme B (for alkenes) below for triazines of formula (I). Inverse electron demand Diels Alder reaction between the compound of formula (I) and an alkyne provides an unstable intermediate that extrudes $N_2$ in a reverse Diels Alder reaction to provide the pyridine product.

Inverse electron demand Diels Alder reaction between the compound of formula (I) and an alkene (a Z-alkene is shown but the reaction also works with E-alkenes) provides an unstable intermediate that extrudes $N_2$ in a reverse Diels Alder reaction to provide a further intermediate. That intermediate is automatically oxidised (e.g. by oxygen in the air or solvent or by biological oxidising agents in the tissue) to provide the pyridine product.

Scheme A

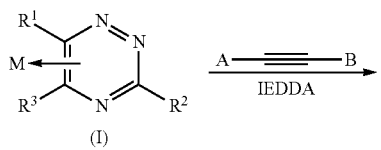

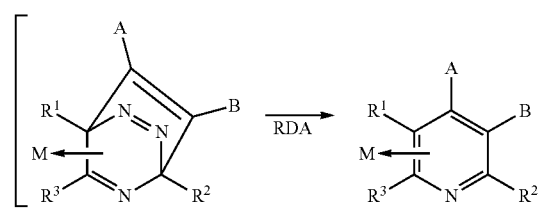

Scheme B

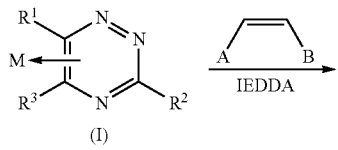

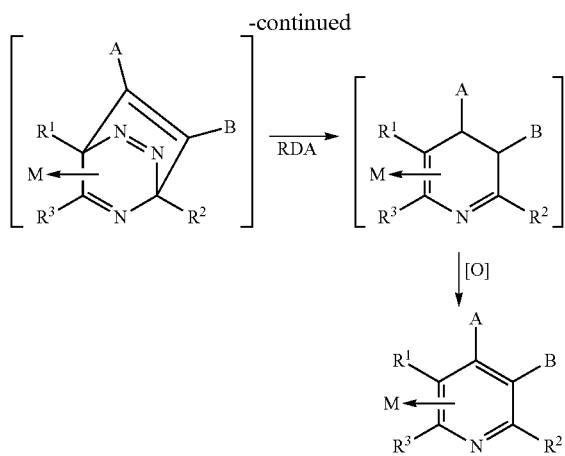

The reaction may be conducted in an organic solvent. The organic solvent may be an aprotic polar organic solvent (e.g. dimethylsulfoxide, dimethylformamide, dimethylacetamide, diethylether, tetrahydrofuran, acetone, dimethylethyleneglycol, chloroform, acetonitrile). The organic solvent may be a protic polar organic solvent (e.g. ethanol, methanol, ethyleneglycol). The organic solvent may be a non-polar organic solvent (e.g. benzene, dichloromethane, dichloroethane, pentane, hexane, cyclohexane, toluene, xanthene, chlorobenzene).

The reaction may be conducted in an aqueous media. The aqueous media may be water. The aqueous media may be a mix of a polar organic solvent (e.g. those listed in the previous paragraph) and water. It may be that the solvent is greater than 10% by volume water, e.g. greater than 25% by volume or greater than 50% by volume water. The aqueous media may be a solution with solutes (e.g. ionic salts, water soluble organic molecules and biopolymers) dissolved within it.

The reaction may be conducted in a biological fluid, e.g. a bodily fluid. The reaction may be conducted in the human or animal body. The reaction may be conducted in a biological sample, e.g. a sample of tissue that has been obtained from a human or animal body. The reaction may be conducted in a living cell.

The reaction may take more than 5 minutes, e.g. more than 30 minutes, to go to the desired level of completion. The reaction may take less than 24 hours, e.g. less than 4 hours to go to the desired level of completion.

Methods of Imaging

The method may be a method of medical imaging or imaging a biological sample.

It may be that the 1,2,4-triazine is attached to a biological targeting moiety. Where this is the case, the method may comprise:
  administering the 1,2,4-triazine to a subject or a biological sample; and
  administering the dienophile to the subject or a biological sample; and
  detecting the image.

It may be that the dienophile (e.g. the alkene or alkyne) is attached to a biological targeting moiety. Where this is the case, the method may comprise:
  administering the dienophile to a subject or a biological sample; and
  administering the 1,2,4-triazine to the subject or a biological sample; and
  detecting the image.

Medical Uses

Also provided is a 1,2,4-triazine for use in medical treatment, wherein said 1,2,4-triazine is complexed to a metal. Typically, in this case the treatment will comprise the delivery of a therapeutic agent to a particular site or tissue using a method of the first aspect.

Also provided is the use of a 1,2,4-triazine in medical imaging, wherein said 1,2,4-triazine is complexed to a metal. Also provided is a 1,2,4-triazine for use in medical imaging, wherein said 1,2,4-triazine is complexed to a metal. Typically, in this case the imaging will comprise the delivery of a imaging agent to a particular site or tissue using a method of the first aspect (and particularly using a method described above under Methods of Imaging).

Where appropriate, any feature described above in relation to the first aspect of the invention applies in particular to these aspects of the invention.

Biological Target

A "biological target" as used in the present invention relates to a target to be detected in a diagnostic and/or imaging method.

The biological target can be selected from any suitable targets within the human or animal body or on a pathogen or parasite, e.g. a group comprising cells such as cell membranes and cell walls, receptors such as cell membrane receptors, intracellular structures such as Golgi bodies or mitochondria, enzymes, receptors, DNA, RNA, viruses or viral particles, antibodies, proteins, carbohydrates, monosaccharides, polysaccharides, cytokines, hormones, steroids, somatostatin receptor, monoamine oxidase, muscarinic receptors, myocardial sympatic nerve system, leukotriene receptors, e.g. on leukocytes, urokinase plasminogen activator receptor (uPAR), folate receptor, apoptosis marker, (anti-) angiogenesis marker, gastrin receptor, dopaminergic system, serotonergic system, GABAergic system, adrenergic system, cholinergic system, opoid receptors, GPIIb/IIIa receptor and other thrombus related receptors, fibrin, calcitonin receptor, tuftsin receptor, integrin receptor, VEGF/EGF receptors, EGF, matrix metalloproteinase (MMP), P/E/L-selectin receptor, LDL receptor, P-glycoprotein, neurotensin receptors, neuropeptide receptors, substance P receptors, NK receptor, CCK receptors, sigma receptors, interleukin receptors, herpes simplex virus tyrosine kinase, human tyrosine kinase.

The biological target may be a protein such as a receptor. The biological target may be an oligosaccharide. Alternatively, the biological target may be a metabolic pathway, which is upregulated during a disease, e.g. infection or cancer, such as DNA synthesis, protein synthesis, membrane synthesis and carbohydrate uptake.

Thus, the biological target and the biological targeting moiety are typically selected so as to result in the targeting of a specific cell type or tissue or manifestation of a disease, e.g. a tumour in cancer or a thrombus in cardiovascular disease. This can be achieved by selecting primary targets with tissue-, cell- or disease-specific expression.

Administration

The methods of the invention may require the administration of two entities to a subject or to a biological sample. The first entity ('pretargeting probe') comprises a biological targeting moiety and either a) a dienophile; or b) the 1,2,4-triazine. The second entity comprises whichever of a) a dienophile; or b) the 1,2,4-triazine is not in the first entity.

For both entities dosage administered will vary with the compound employed, the mode of administration and the size and location of the biological target indicated. Both entities will generally be administered in the form of a pharmaceutically acceptable composition in which the entity, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

The compositions may be administered topically (e.g. to the skin) in the form, e.g., of creams, gels, lotions, solutions, suspensions, or systemically, e.g. by oral administration in the form of tablets, capsules, syrups, powders, suspensions, solutions or granules; or by parenteral administration in the form of a sterile solution, suspension or emulsion for injection (including intravenous, subcutaneous, intramuscular, intravascular or infusion); or by rectal administration in the form of suppositories; or by inhalation (i.e. in the form of an aerosol or by nebulisation).

For oral administration the compounds may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound may be filled into hard gelatine capsules. Liquid preparations for oral application may be in the form of syrups or suspensions, for example, solutions containing the compound, the balance being sugar and a mixture of ethanol, water, glycerol and propylene glycol. Optionally such liquid preparations may contain colouring agents, flavouring agents, sweetening agents (such as saccharine), preservative agents and/or carboxymethyl-cellulose as a thickening agent or other excipients known to those skilled in art.

For intravenous (parenteral) administration the compounds may be administered as a sterile aqueous or oily solution.

Kits

In a second aspect of the invention is provided a kit for medical imaging or for imaging a biological sample, the kit comprising:
    a 1,2,4-triazine; and
    a dienophile;
wherein the 1,2,4-triazine is complexed to the metal; and
wherein either:
A) the 1,2,4-triazine is attached to a biological targeting moiety; or
B) the dienophile is attached to a biological targeting moiety.

It may be that the 1,2,4-triazine is comprised in a pharmaceutically acceptable formulation also comprising at least one pharmaceutical excipient. It may be that the 1,2,4-triazine is in a form suitable for dissolving in an aqueous media prior to administration.

It may be that the dienophile is comprised in a pharmaceutically acceptable formulation also comprising at least one pharmaceutical excipient. It may be that the dienophile is in a form suitable for dissolving in an aqueous media prior to administration.

Where appropriate, any feature described above in relation to the first aspect of the invention applies in particular to the second aspect of the invention. This is particularly the case for the embodiments described above under the headings: Triazines, Dienophiles, Metal, Biological targeting moiety and Administration.

The invention may be as described in the following numbered paragraphs:
1. A method of forming a pyridine, said pyridine being complexed to a metal; the method comprising:
    contacting a 1,2,4-triazine with a dienophile to form a pyridine;
wherein both the 1,2,4-triazine starting material and the pyridine product material are complexed to the metal.
2. A method of paragraph 1, wherein the 1,2,4-triazine is of formula (I):

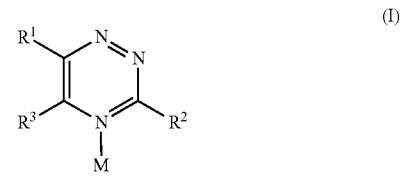

wherein M is the metal, which may be bonded to other ligands;
$R^1$, $R^2$ and $R^3$ are each independently selected from H, $C_1$-$C_6$-alkyl, $C_1$-$C_6$-haloalkyl, $C_3$-$C_6$-alkenyl, $C_1$-$C_6$-alkynyl, halo, nitro, cyano, $C(O)R_4$, $(CH_2)_nCO_2R^4$, $OR^4$, $SR^4$, $NR^4R^5$, $C(O)NR^4R^4$, $S(O)R^4$, $S(O)_2R^4$, $C_3$-$C_6$-cycloalkyl, 3-18-membered heterocycloalkyl, 5-, 6-, 9-, or 10-membered heteroaryl, phenyl and naphthyl;
wherein if any of $R^1$, $R^2$ and $R^3$ are $C_1$-$C_6$-alkyl, $C_3$-$C_6$-cycloalkyl, 3-6-membered heterocycloalkyl, 5-, 6-, 9-, or 10-membered heteroaryl, phenyl, naphthyl that group can be substituted with from 1 to 5 $R^6$ groups;
$R^4$ is independently at each occurrence selected from H and $C_1$-$C_4$-alkyl; and
$R^5$ is independently at each occurrence selected from H, $C_1$-$C_4$-alkyl, $C(O)$—$C1$-$C_4$-alkyl and $S(O)_2$—$C_1$-$C_4$-alkyl;
$R^6$ is selected from 5-, 6-, 9-, or 10-membered heteroaryl, phenyl, naphthyl, $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $C(O)NR^4R^4$, $S(O)R^4$ and $S(O)_2R^4$;
    wherein if $R^6$ is $C_1$-$C_6$-alkyl, 5-, 6-, 9-, or 10-membered heteroaryl, phenyl, or naphthyl, $R^6$ can be substituted with from 1 to 5 $R^7$ groups;
$R^7$ is selected from 5-, 6-, 9-, or 10-membered heteroaryl, phenyl, naphthyl, $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $C(O)NR^4R^4$, $S(O)R^4$ and $S(O)_2R^4$;
    wherein if $R^7$ is $C_1$-$C_6$-alkyl, 5-, 6-, 9-, or 10-membered heteroaryl, phenyl, or naphthyl then $R^7$ can be substituted with from 1 to 5 $R^8$ groups;
$R^8$ is selected from $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $C(O)NR^4R^4$, $S(O)R^4$ and $S(O)_2R_4$;

wherein the 1,2,4-triazine is optionally attached to a biological targeting moiety via one of the alkyl, $C_3$-$C_6$-alkenyl, $C_1$-$C_6$-alkynyl, $C_3$-$C_6$-cycloalkyl, 3-6-membered heterocycloalkyl, 5-, 6-, 9-, or 10-membered heteroaryl, phenyl, naphthyl groups mentioned above;

n is independently at each occurrence an integer selected from 0, 1 and 2;

where any of $R^6$, $R^7$ or $R^8$ are phenyl, said phenyl group may be bonded to the metal;

where any of $R^6$, $R^7$ or $R^8$ are $SR^4$, $NR^4R^5$, $(CH_2)_n COOR^4$ or $OR^4$, $R^4$ may be absent and the heteroatom (S, N or O) may be bonded to the metal.

3. A method of paragraph 2, wherein $R^3$ is a 5-, 6-, 9-, or 10-membered heteroaryl group.

4. A method of paragraph 2, wherein $R^3$ is a 2-pyridyl group.

5. A method of any one of paragraphs 2 to 4, wherein $R^2$ is H.

6. A method of any one of paragraphs 2 to 5, wherein $R^1$ is H.

7. A method of any preceding paragraph wherein the dienophile is a $C_3$-$C_{10}$-cycloalkene or $C_7$-$C_{10}$-cycloalkyne.

8. A method of any preceding paragraph wherein the metal is selected from Ru, Ir, Eu, Gd, Tb, Pt, Re, Tc, Zn.

9. A method of any preceding paragraph wherein the metal is complexed to one or more ligands other than the triazine.

10. A method of any preceding paragraph wherein the 1,2,4-triazine is attached to a biological targeting moiety.

11. A method of paragraph 10, wherein the method is a method of medical imaging or imaging a biological sample and wherein the 1,2,4-triazine is attached to a biological targeting moiety and the method comprises:
    administering the 1,2,4-triazine to a subject or a biological sample; and
    administering the dienophile to the subject or a biological sample; and
    detecting the image.

12. A method of any one of paragraphs 1 to 19, wherein the alkene or alkyne is attached to a biological targeting moiety.

13. A method of paragraph 12, wherein the method is a method of medical imaging or imaging a biological sample and wherein the dienophile is attached to a biological targeting moiety and the method comprises:
    administering the dienophile to a subject or a biological sample; and
    administering the 1,2,4-triazine to the subject or a biological sample; and
    detecting the image.

14. A kit for medical imaging or for imaging a biological sample, the kit comprising:
    a 1,2,4-triazine; and
    a dienophile;
wherein the 1,2,4-triazine is complexed to a metal; and
wherein either:
A) the 1,2,4-triazine is attached to a biological targeting moiety; or
B) the dienophile is attached to a biological targeting moiety.

15. A kit of paragraph 14, wherein the 1,2,4-triazine is of formula (I):

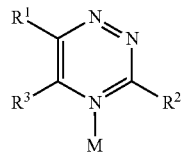

(I)

wherein M is the metal, which may be bonded to other ligands;

$R^1$, $R^2$ and $R^3$ are each independently selected from H, $C_1$-$C_6$-alkyl, $C_1$-$C_6$-haloalkyl, $C_3$-$C_6$-alkenyl, $C_1$-$C_6$-alkynyl, halo, nitro, cyano, $C(O)R_4$, $(CH_2)_nCO_2R^4$, $OR^4$, $SR^4$, $NR^4R^5$, $C(O)NR^4R^4$, $S(O)R^4$, $S(O)_2R^4$, $C_3$-$C_6$-cycloalkyl, 3-18-membered heterocycloalkyl, 5-, 6-, 9-, or 10-membered heteroaryl, phenyl and naphthyl;

wherein if any of $R^1$, $R^2$ and $R^3$ are $C_1$-$C_6$-alkyl, $C_3$-$C_6$-cycloalkyl, 3-6-membered heterocycloalkyl, 5-, 6-, 9-, or 10-membered heteroaryl, phenyl, naphthyl that group can be substituted with from 1 to 5 $R^6$ groups;

$R^4$ is independently at each occurrence selected from H and $C_1$-$C_4$-alkyl; and $R^5$ is independently at each occurrence selected from H, $C_1$-$C_4$-alkyl, $C(O)$—$C_1$-$C_4$-alkyl and $S(O)_2$—$C_1$-$C_4$-alkyl;

$R^6$ is selected from 5-, 6-, 9-, or 10-membered heteroaryl, phenyl, naphthyl, $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $C(O)NR^4R^4$, $S(O)R^4$ and $S(O)_2R^4$;

wherein if $R^6$ is $C_1$-$C_6$-alkyl, 5-, 6-, 9-, or 10-membered heteroaryl, phenyl, or naphthyl, $R^6$ can be substituted with from 1 to 5 $R^7$ groups;

$R^7$ is selected from 5-, 6-, 9-, or 10-membered heteroaryl, phenyl, naphthyl, $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $C(O)NR^4R^4$, $S(O)R^4$ and $S(O)_2R^4$;

wherein if $R^7$ is $C_1$-$C_6$-alkyl, 5-, 6-, 9-, or 10-membered heteroaryl, phenyl, or naphthyl then $R^7$ can be substituted with from 1 to 5 $R^8$ groups;

$R^8$ is selected from $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $C(O)NR^4R^4$, $S(O)R^4$ and $S(O)_2R^4$;

wherein the 1,2,4-triazine is optionally attached to a biological targeting moiety via one of the alkyl, $C_3$-$C_6$-alkenyl, $C_1$-$C_6$-alkynyl, $C_3$-$C_6$-cycloalkyl, 3-18-membered heterocycloalkyl, 5-, 6-, 9-, or 10-membered heteroaryl, phenyl, naphthyl groups mentioned above;

n is independently at each occurrence an integer selected from 0, 1 and 2;

where any of $R^6$, $R^7$ or $R^8$ are phenyl, said phenyl group may be bonded to the metal;

where any of $R^6$, $R^7$ or $R^8$ are $SR^4$, $NR^4R^5$, $(CH_2)_n COOR^4$ or $OR^4$, $R^4$ may be absent and the heteroatom (S, N or O) may be bonded to the metal.

16. A kit of paragraph 15, wherein $R^3$ is a 5-, 6-, 9-, or 10-membered heteroaryl group.

17. A kit of paragraph 15, wherein $R^3$ is a 2-pyridyl group.

18. A kit of any one of paragraphs 15 to 17, wherein $R^2$ is H.

19. A kit of any one of paragraphs 15 to 18, wherein $R^1$ is H.

20. A kit of any one of paragraphs 14 to 19 wherein the dienophile is a $C_3$-$C_{10}$-cycloalkene or $C_5$-$C_{10}$-cycloalkyne.

21. A kit of any one of paragraphs 14 to 20 wherein the metal is selected from Ru, Ir, Eu, Gd, Tb, Pt, Re, Tc, Zn.

22. A kit of any one of paragraphs 14 to 21 wherein the metal is complexed to one or more ligands other than the triazine.

23. A kit of any one of paragraphs 14 to 22 wherein the 1,2,4-triazine is attached to a biological targeting moiety.

24. A kit of any one of paragraphs 14 to 22, wherein the alkene or alkyne is attached to a biological targeting moiety.

Definitions

The term $C_m$-$C_n$ refers to a group with m to n carbon atoms.

The term "alkyl" refers to a linear or branched hydrocarbon chain. For example, $C_1$-$C_6$-alkyl may refer to methyl, ethyl, n-propyl, iso-propyl, n-butyl, sec-butyl, tert-butyl, n-pentyl and n-hexyl. The alkyl groups may be unsubstituted.

The term "haloalkyl" refers to a hydrocarbon chain substituted with at least one halogen atom independently chosen at each occurrence from: fluorine, chlorine, bromine and iodine. The halogen atom may be present at any position on the hydrocarbon chain. For example, $C_1$-$C_6$-haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A halo alkyl group may be a fluoroalkyl group, i.e. a hydrocarbon chain substituted with at least one fluorine atom.

The term "alkenyl" refers to a branched or linear hydrocarbon chain containing at least one double bond. The double bond(s) may be present as the E or Z isomer. The double bond may be at any possible position of the hydrocarbon chain. For example, "$C_2$-$C_6$-alkenyl" may refer to ethenyl, propenyl, butenyl, butadienyl, pentenyl, pentadienyl, hexenyl and hexadienyl. The alkenyl groups may be unsubstituted. "Alkene carbon" refers to one of the $sp^2$ hybridised carbons that makes up the double bond.

The term "alkynyl" refers to a branched or linear hydrocarbon chain containing at least one triple bond. The triple bond may be at any possible position of the hydrocarbon chain. For example, "$C_2$-$C_6$-alkynyl" may refer to ethynyl, propynyl, butynyl, pentynyl and hexynyl. The alkynyl groups may be unsubstituted.

The term "cycloalkyl" refers to a saturated hydrocarbon ring system containing 3, 4, 5 or 6 carbon atoms. For example, "$C_3$-$C_6$-cycloalkyl" may refer to cyclopropyl, cyclobutyl, cyclopentyl, cyclohexyl. The cycloalkyl groups may be unsubstituted.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. For example, "monocyclic aryl" may be phenyl and "polycyclic aryl" may refer to naphthyl, anthracenyl, phenanthrenyl and pyrenyl. The aryl group may be unsubstituted.

The term "heteroaryl" may refer to any aromatic (i.e. a ring system containing (4n+2) π-electrons or n-electrons in the π-system) 5-14 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 1-4 heteroatoms independently selected from O, S and N; and 6-membered heteroaryl groups in which the heteroaromatic ring is substituted with 1-3 (e.g. 1-2) nitrogen atoms; 9-membered bicyclic heteroaryl groups in which the heteroaromatic system is substituted with 1-4 heteroatoms independently selected from O, S and N; 10-membered bicyclic heteroaryl groups in which the heteroaromatic system is substituted with 1-4 nitrogen atoms; 14-membered tricyclic heteroaryl groups in which the heteroaromatic system is substituted with 1-4 nitrogen atoms. Specifically, heteroaryl groups may be independently selected from: pyrrole, furan, thiophene, pyrazole, imidazole, oxazole, isoxazole, triazole, oxadiazole, thiadiazole, tetrazole; pyridine, pyridazine, pyrimidine, pyrazine, triazine, indole, isoindole, benzofuran, isobenzofuran, benzothiophene, indazole, benzimidazole, benzoxazole, benzthiazole, benzisoxazole, purine, quinoline, isoquinoline, cinnoline, quinazoline, quinoxaline, pteridine, phthalazine, naphthyridine. Heteroaryl groups may also be 6-membered heteroaryl groups in which the heteroaromatic ring is substituted with 1 heteroatomic group independently selected from O, S and NH and the ring also comprises a carbonyl group. Such groups include pyridones and pyranones. The heteroaryl system itself may be substituted with other groups. The heteroaryl group may be unsubstituted.

EXAMPLES 5-(furan-2-yl)-3-(pyridine-2-yl)-1,2,4-triazine (DVS-35)

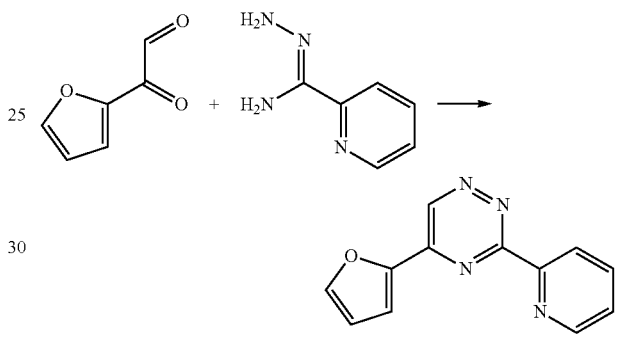

A mixture of 2-(furan-2-yl)-2-oxoacetaldehyde (15 mmol) and (Z)-picolinohydrazonamide (2.0 g, 15 mmol) in ethanol (100 mL) was heated under reflux for 3 hours. All volatiles were removed by rotary evaporation under reduced pressure. The residue was then triturated with water and the formed solid was filtered off, washed with water and dried. Yield 2.3 g (70%). The product was used without further purification. M.p. 92° C. $^1$H NMR (CDCl$_3$, 400 MHz): δ 9.56 (s, 1H), 8.89 (d, 1H, J=4.7 Hz), 8.63 (t, 1H, J=8.3 Hz), 7.97-7.87 (m, 1H), 7.78-7.70 (m, 1H), 7.67 (d, 1H, J=3.5 Hz), 7.53-7.43 (m, 1H), 6.74-6.64 (m, 1H).

3-(pyridin-2-yl)-1,2,4-triazine-5-carboxylic acid (DVS-42)

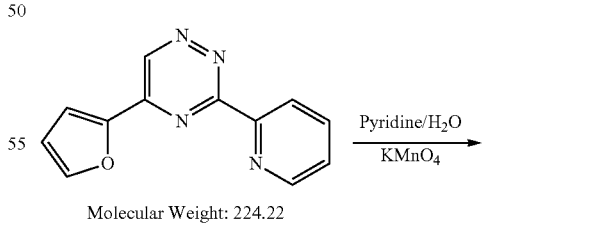

Molecular Weight: 224.22

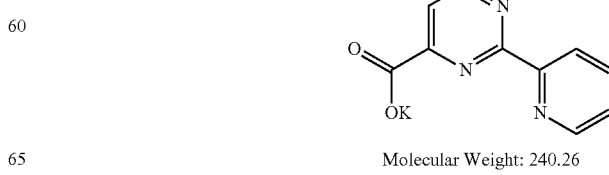

Molecular Weight: 240.26

The triazine DVS-35 (4.88 g, 21.7 mmol) was dissolved in pyridine (20 mL) and then water (200 mL) was added. To this solution, at stirring at room temperature, potassium permanganate (13.8 g, 87 mmol) was added in small (0.5 g) portions over a period of 2 hours. The temperature of the reaction mixture was kept below 55° C. The mixture was filtered and the filtrate was evaporated to dryness. The product was then recrystallized from a small amount of water and dried at room temperature overnight. (It should be noted that the filtrate contains a big amount of the product). Yield 0.97 g (19%). $^1$H NMR (D$_2$O, 400 MHz): δ 9.55 (s, 1H), 8.62 (d, 1H, J=4.6 Hz), 8.39 (d, 1H, J=7.8 Hz), 7.98 (t, 1H, J=7.8, 7.2 Hz), 7.54 (t, 1H, J=4.6, 7.2 Hz); IR, ν, cm$^{-1}$: 1627 (C=O).

VNK-246

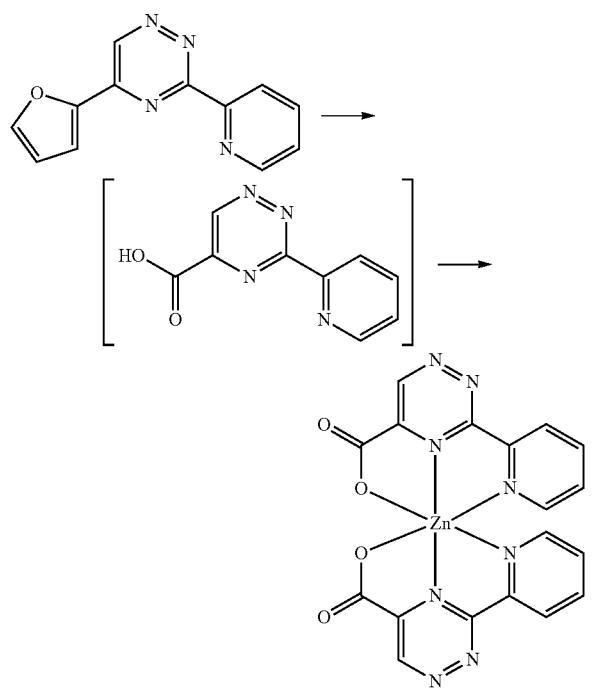

DVS-35 (1.25 g, 5.6 mmol) was dissolved in a mixture of water/pyridine (10/1v/v) at 50° C. At this solution, at stirring, potassium permanganate (3.7 g, 23.4 mmol, 4.18 eq.) was added in portions of approx. 0.3 g over a period of 30 min. The mixture was then stirred at 50-60° C. for 30 min and filtered while still hot. The dark solid from the filter (MnO$_2$) was placed in a beaker and water (100 mL) was added. The suspension was stirred and heated to 90° C. and then filtered. All filtrates were combined and all volatiles were removed by rotary evaporation under reduced pressure. The residue was dissolved in 20 mL of water and 3M HCl was added dropwise (gas evolution) till slightly acidic pH. After that, a solution of zinc sulphate in water (excess) was added, the mixture was heated to 70° C. and then left overnight. Precipitated solid was filtered off, washed with water (3×10 mL) and acetone (3×5 mL) to give VNK-246 as yellow solid. Yield 570 mg (44%). $^1$H NMR (DMSO-D$_6$, 400 MHz): δ$_H$ 10.21 (s, 1H), 8.89 (d, 1H, J=7.6 Hz), 8.42 (d, 1H, J=4.6 Hz), 8.27 (t, 1H, J=7.2, 8.0 Hz), 7.68 (t, 1H, J=4.6, 7.2 Hz).

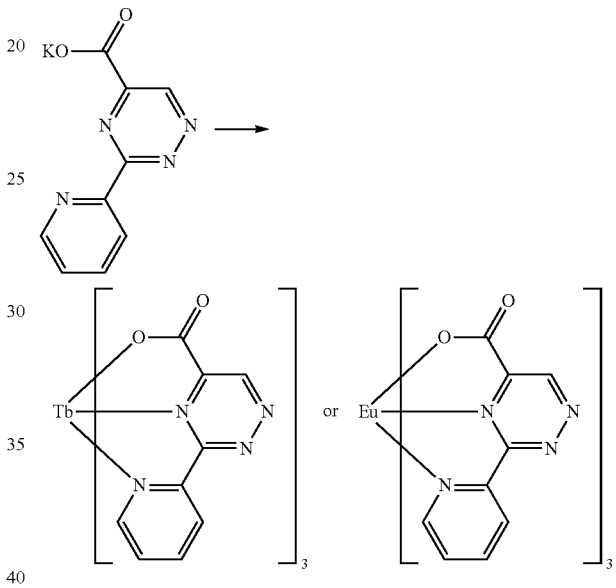

A solution of terbium chloride (1 eq) or europium chloride in water was added to a solution of the starting potassium salt of the triazine ligand (3 eq) in water. The mixture was stirred at 55° C. for 2 days. The mixture was allowed to cool to room temperature and the solid was filtered off to give the target complex.

Preparation of VNK-405, VNK-406, VNK-408, VNK-421, VNK-423, and VNK-548

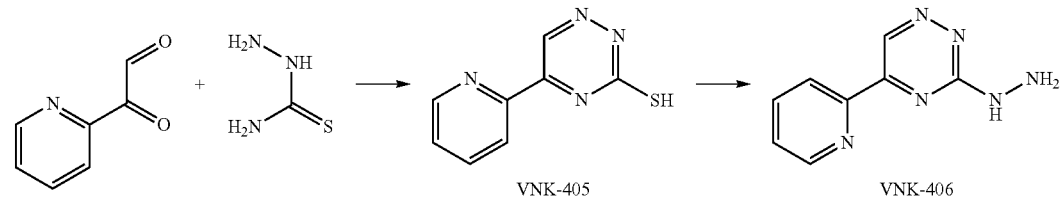

-continued

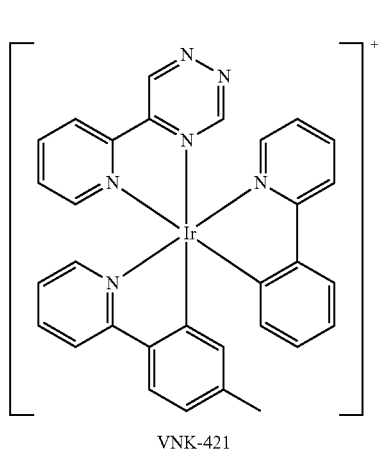

VNK-421

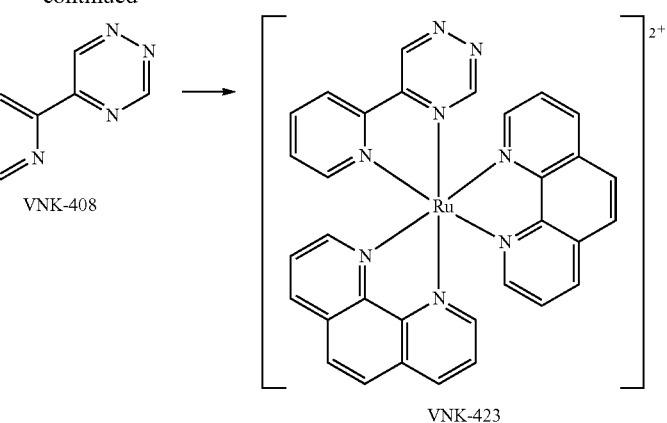

VNK-408

VNK-423

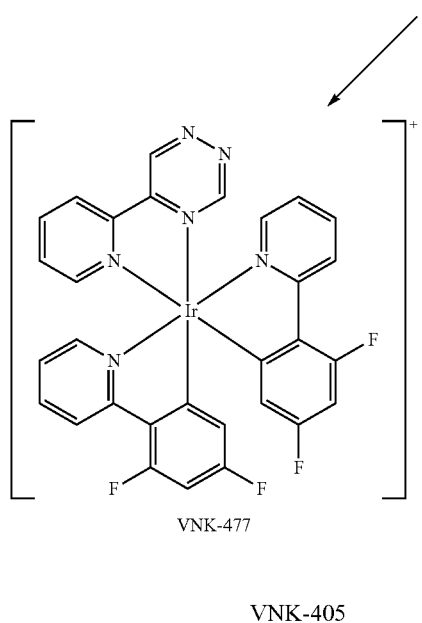

VNK-477

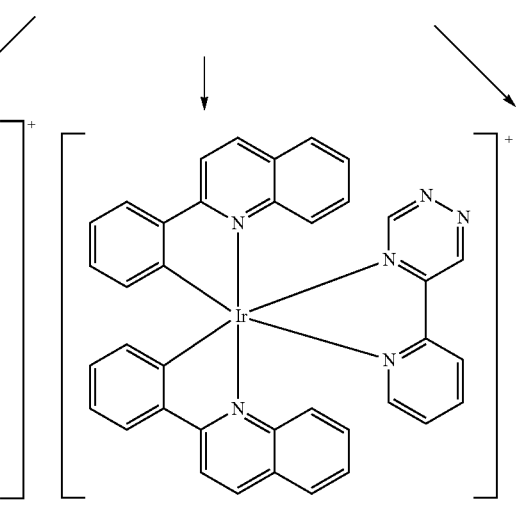

VNK-527

VNK-548

VNK-405

To a solution of 2-oxo-2-(pyridin-2-yl)acetaldehyde (100 mmol) in a mixture of DMSO (100 mL) and water (200 mL), potassium carbonate (200 mmol) and thiosemicarbazide (9.1 g, 100 mmol) were added and the reaction mixture was stirred at RT for 30 minutes. The mixture was then warmed up to 50-60° C. and stirred at this temperature for 1 hour. The mixture was then neutralised by addition of an excess of acetic acid casing a formation of the solid. The solid was filtered off, washed with water and dried in oven. Yield 11.3 g (59%). $^1$H NMR (400 MHz, DMSO-D$_6$): δ 9.08 (s, 1H), 8.81 (br.d, J=4.6 Hz, 1H), 8.34 (d, J=7.7 Hz, 1H), 8.06 (br.t, J=7.7 Hz, 1H) 7.68 (dd, J=7.7, 4.6 Hz, 1 H).

VNK-406

A mixture of VNK-405 (11.1 g, 58.4 mmol) and hydrazine hydrate (14.6 g, 292 mmol, 5 eq) was heated under reflux for 15 minutes (solid formed). Methanol (20 mL), water (20 mL) and acetic acid (10 mL) were added. The solid was filtered off, washed with water (30 mL) and methanol (30 mL). Yield 5.96 g (54%). $^1$H NMR (400 MHz, DMSO-D$_6$): δ 9.36 (s, 1H), 8.88 (br.s, 1H), 8.74 (br.d, J=4.6 Hz, 1H), 8.40 (br.s, 1H), 8.02 (ddd, J=7.8, 7.8, 1.8, 1H), 7.59 (m, 1H), 4.45 (s, 2H).

VNK-408

A mixture of VNK-406 (940 mg, 5 mmol), methanol (100 mL) and sodium methoxide (2.7 g, 50 mmol) was stirred at 75° C. (bath temperature) for 14 hours. Acetic acid (5 mL) and water (20 mL) were added and the mixture was evaporated to a volume of approximately 15 mL. The mixture was basified by addition of 33% aqueous ammonia (5 mL). Precipitated solid was filtered off, washed with water (20 mL) and dried. Yield 526 mg (67%). $^1$H NMR (400 Hz, CDCl$_3$): δ 10.30 (d, J=1.8 Hz 1H), 9.71 (d, J=1.8 Hz 1H), 8.79 (br.d, J=4.6 Hz, 1H), 8.54 (d, J=7.8 Hz, 1H), 7.92 (ddd, J=7.8, 7.8, 1.8, 1H), 7.49 (dd, J=7.4, 4.6 Hz, 1 H). $^{13}$C NMR (100 MHz, CDCl$_3$): δ 157.3, 154.0, 151.7, 150.1, 147.4, 137.5, 126.7, 122.9.

VNK-421 Chloride

A mixture of [(tpy)$_2$Ir(μ-Cl)]$_2$ VNK-411 (226 mg, 0.4 mmol for Ir), VNK-408 (90 mg, 0.6 mmol, 1.5 eq), chloroform (10 mL) and methanol (10 mL) was heated under reflux for 2 hours. The solvent was evaporated. The product was purified by column chromatography using silica gel as a stationary phase and a mixture of DCM/methanol mixture 5/1, v/v as an eluent. A green fraction was collected. The solvent was evaporated and the residue was dissolved in DCM (2 mL). To this solution, ether (20 mL) was added causing the formation of a solid. The solid was filtered off, washed with ether to give VNK-421RR chloride. Yield 202 mg (70%). $^{13}$C NMR (100 MHz, CDCl$_3$): δ 167.7, 167.2, 155.3, 154.9, 151.7, 151.3, 149.7, 149.6, 149.5, 148.8, 146.9, 141.6, 141.4, 141.1, 140.6, 140.5, 138.7, 138.6, 132.6, 132.1, 131.3, 125.1, 124.9, 124.7, 124.6, 123.5, 123.4, 119.7, 119.5, 22.0

VNK-527

A mixture of [Ir(pqi)2]Cl2 VNK-525 (221 mg, 0.35 mmol for Ir) and VNK-502B (64 mg, 0.41 mmol, 1.15 eq) in chloroform (10 mL) and methanol (10 mL) was heated under reflux for 14 hours. The solvent was evaporated by rotary evaporation to a volume of approximately 2 mL. Diethyl ether (25 mL) was added causing formation of a solid. The solid was filtered off, washed with ether. The product was purified by column chromatography using silica gel as stationary phase and a mixture of DCM/MeOH 20/1 as a mobile phase. Yield 75 mg (27%).

VNK-423

A mixture of bis(1,10-phenanthroline)dichlororuthenium (II) (212 mg, 0.4 mmol), VNK-408 (80 mg, 0.51 mmol, 1.27 eq) in 6 mL of water was heated in a microwave oven at 120° C. (150 W max.), for 70 min. The aqueous mixture was washed with DCM in a separating funnel (3×15 ml). To the aqueous layer, saturated solution of NaPF$_6$ (6 mL) was added causing the formation of amorphous precipitate. DCM (50 mL) was added, but it does not dissolve the solid completely. The DCM and organic layers were drained. The residue was treated with water and mechanically removed from the sides of the separating funnel. The solid was filtered off, washed with water and little amount of ethanol. Yield 84 mg (17%). $^1$H NMR (400 Hz, acetine-D$_6$): δ 10.48 (br.s, 1H), 9.35 (br.s, 1H), 9.21 (d, J=8.0 Hz, 1H), 8.87 (d, J=8.0 Hz, 2H), 8.71-8.81 (m, 4H), 8.18-8.43 (m, 10H), 7.91-7.98 (m, 2H), 7.71-7.80 (m, 2 H), 7.65 (t, J=6.8 Hz, 1H).

VNK-548

To a solution of the triazine VNK-408 (158 mg, 1 mmol) in toluene (15 mL), Re(CO)$_5$Cl (360 mg, 1 mmol) was added and the mixture was heated under reflux for 2 hours. The mixture was allowed to cool to RT. The solid was filtered off, washed with toluene and petrol ether to give VNK-548. Yield 406 mg (87%) $^1$H NMR (400 Hz, DMSO-D$_6$): δ 10.70 (s, 1H), 10.22 (s, 1H), 9.20 (d, J=4.6 Hz, 1H), 8.51 (d, J=7.8 Hz, 1H), 8.26 (t, J=7.8, 1H), 7.81 (dd, J=7.4, 4.6 Hz, 1 H). $^{13}$C NMR (100 MHz, DMSO-D$_6$): δ 197.7, 196.4, 188.2, 157.8, 155.1, 154.7, 152.2, 149.0, 141.1, 131.5, 128.2.

Preparation of VNK-479, VNK-480, VNK-481, VNK-482, VNK-483R, VNK-514, and VNK-515

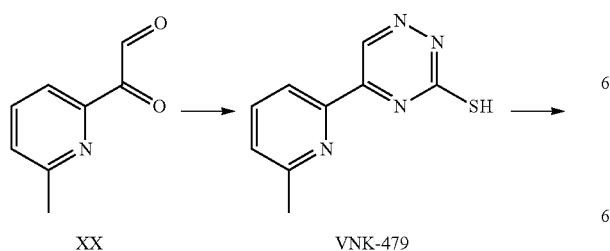

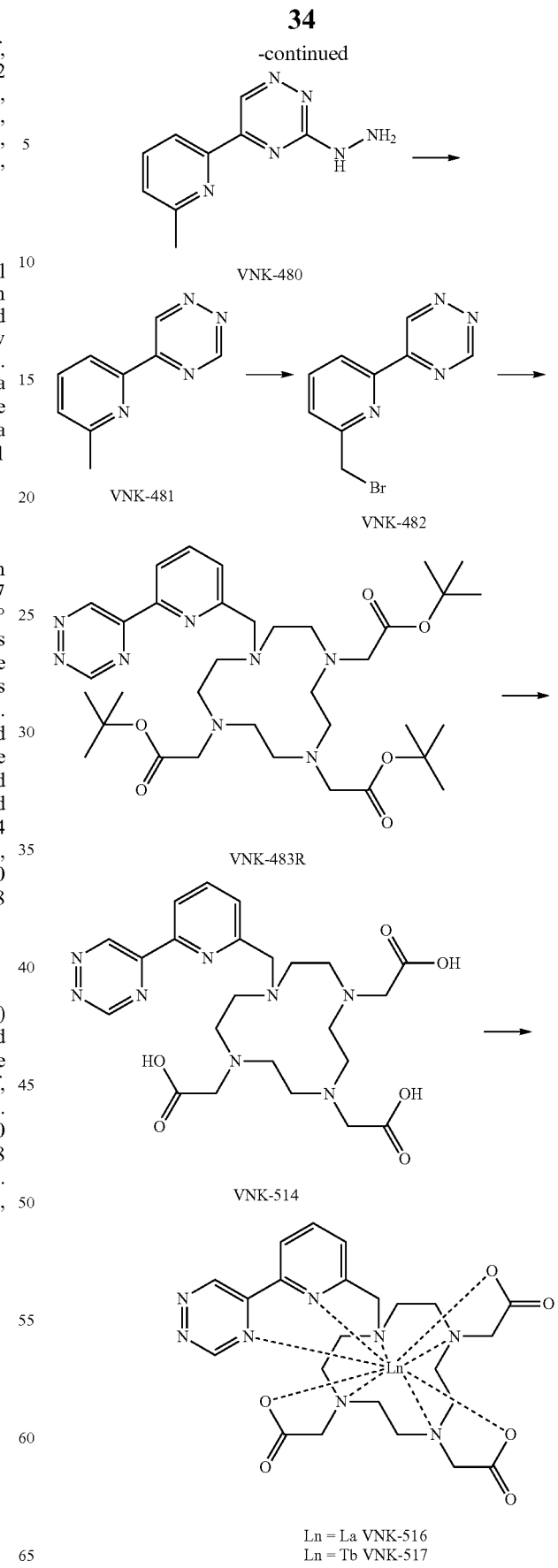

3-mercapto-5-(6-methylpyrinin-2-yl)-1,2,4-triazine VNK-479

To a solution of the dicarbonyl XX (74 mmol) in DMSO (74 mL) and water (150 mL), thiosemicarbazide (6.73 g, 74 mmol) and $Na_2CO_3$ (7.7 g, 74 mmol) were added and the mixture was stirred at RT for 10 minutes. The mixture was then warmed up to 50-60° C. and stirred at this temperature for 1 hour. The mixture was then filtered and the filtrate was neutralised by careful addition of acetic acid. The formed red solid was filtered off, washed with water and dried at room temperature for 14 hours and then at 100° C. for 30 min. Yield 7.6 g (50%). This product was used without further purification. Small amount of the product was recrystallised from ethanol to prepare analytically pure sample. $^1$H NMR (400 MHz, DMSO-$D_6$): δ 9.06 (s, 1H), 8.14 (d, J=7.7 Hz, 1H), 7.93 (t, J=7.7 Hz, 1H), 7.54 (d, J=7.7, 1 H), 2.57 (s, 3H). $^{13}$C NMR (400 MHz, DMSO-$D_6$): δ 181.6, 159.3, 156.8, 150.2, 138.7, 135.7, 127.8, 121.3, 24.6.

3-hydrazino-5-(6-methylpyrinin-2-yl)-1,2,4-triazine VNK-480

To a suspension of VNK-479 (6.12 g, 30 mmol) in ethanol (30 mL), hydrazine hydrate (3 g, 60 mmol, 2 eq) was added. The mixture was heated under reflux for 1 hour. More of hydrazine (2.3 g, 46 mmol) was added. Ethanol was distilled off, the temperature of the reaction mixture was around 100° C. Water (30 mL) was added. The formed solid was filtered off and washed with water. Yield 2.6 g (42%). $^1$H NMR (400 MHz, DMSO-$D_6$): δ 9.34 (s, 1H), 8.87 (br.s, 1H, NH), 8.21 (br. d, J=7.7 Hz, 1H), 7.90 (t, J=7.7 Hz, 1H), 7.44 (d, J=7.7, 1 H), 4.56 (br.s, 2H, $NH_2$), 2.55 (s, 3H). $^{13}$C NMR (400 MHz, DMSO-$D_6$): δ 164.0, 158.9, 154.0, 151.9, 138.4, 137.6, 126.6, 120.0, 24.6.

5-(6-methylpyrinin-2-yl)-1,2,4-triazine VNK-481

A mixture of VNK-480 (1020 mg, 5 mmol), methanol (100 mL) and sodium methoxide (2.7 g, 50 mmol) was stirred at 75° C. (bath temperature) for 14 hours. Acetic acid (5 mL) and water (100 mL) were added and the mixture was extracted with DCM (3×30 mL). Organic layer was washed with saturated solution of sodium bicarbonate, dried over $MgSO_4$. This solution (approx. 90 mL) was applied to a column of silica gel (50 g). The column was then eluted with a DCM/ethyl acetate mixture (5/1, v/v) collecting the first yellow fraction. The solvent was removed by rotary evaporation, the residue was suspended in petrol ether (5 mL) and filtered to give after drying the desired product. Yield 440 mg (51%). $^1$H NMR (400 Hz, $CDCl_3$): δ 10.29 (d, J=2.0 Hz, 1H), 9.68 (d, J=2.0 Hz, 1H), 8.31 (d, J=7.7 Hz, 1H), 7.77 (t, J=7.7 Hz, 1H), 7.33 (d, J=7.7 Hz, 1H), 2.66 (s, 3H). $^{13}$C NMR (400 MHz, $CDCl_3$): δ 159.2, 157.3, 154.2, 151.0, 147.7, 137.6, 126.4, 120.0, 24.6.

5-(6-(Bromomethyl)pyridin-2-yl)-1,2,4-triazine VNK-482

N-Bromosuccinimide (161 mg, 0.91 mmol) and AIBN (17 mg, 0.1 mmol) were added to a solution of VNK-481 (172 mg, 1 mmol) in $CCl_4$ (15 mL) under argon. The reaction mixture was stirred under reflux and irradiation with a (20 W) halogen lamp for 2 hours. The mixture was then applied to a column of dry silica gel and eluded first with DCM, followed by a mixture of DCM/ethyl acetate 5/1 v/v. The first yellow fraction contained the product of dibromination. The second yellow fraction was the desired product. Yield 61 mg (24%). The third fraction is unreacted starting material. $^1$H NMR (400 Hz, $CDCl_3$): δ 10.32 (d, J=2.0 Hz, 1H), 9.72 (d, J=2.0 Hz, 1H), 8.46 (d, J=7.7 Hz, 1H), 7.93 (t, J=7.7 Hz, 1H), 7.65 (d, J=7.7 Hz, 1H), 4.65 (s, 2H). $^{13}$C NMR (400 MHz, $CDCl_3$): δ 157.6, 157.3, 153.5, 151.5, 147.5, 138.7, 126.5, 122.1, 33.2.

VNK-483R

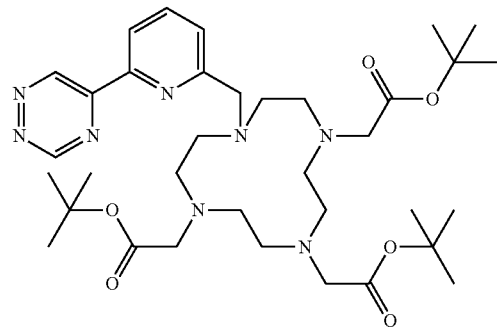

VNK-483R

A mixture of VNK-482 (200 mg, 0.8 mmol) and tri-tert-butyl ester (475 mg, 0.8 mmol), acetonitrile (50 mL) and potassium carbonate (552 mg, 4 mmol) heated under reflux for 14 hours. The mixture was filtered by suction filtration. The filtrate was applied to a short (10 cm, diameter 2.5 cm) column of silica gel, without evaporation of the solvent. The column was firstly eluted with acetonitrile (50 mL) followed by a mixture of acetonitrile/MeOH, 5/1, v/v. The yellow fraction was collected and evaporated to dryness to give VNK-483R (250 mg) as an amorphous solid. The product was used in the next step without further purification.

VNK-514

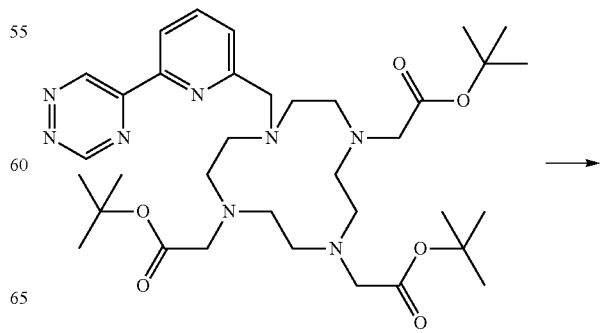

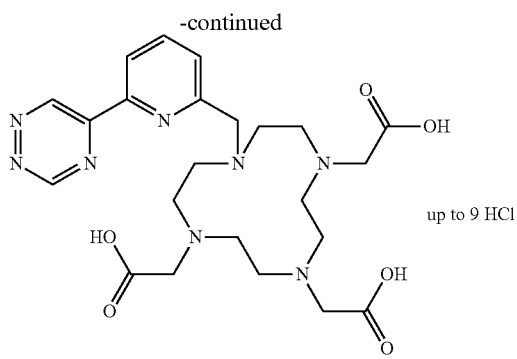

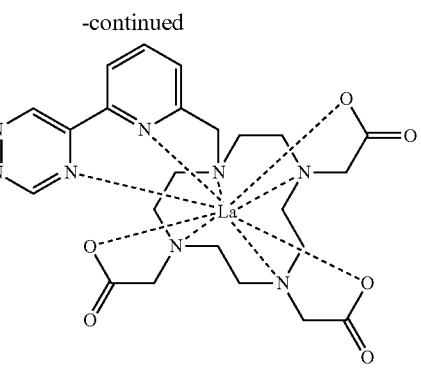

652.4 g/mol

VNK-516

VNK-483R (250 mg) was dissolved in 10 mL of 6M HCl. The solution was stirred overnight and then evaporated to dryness. The residue was triturated with acetone and the solid was filtered off, washed with diethyl ether to give VNK-514. $^1$H NMR (400 Hz, D2O): δ 10.27 (d, J=2.0 Hz, 1H), 9.91 (d, J=2.0 Hz, 1H), 8.64 (d, J=7.7 Hz, 1H), 8.30 (t, J=7.7 Hz, 1H), 7.99 (d, J=7.7 Hz, 1H), 4.93-5.01 (m, 8H), 3.1-3.9 (m, 16H).

VNK-516

VNK-514 (81 mg, 0.1 mmol) was dissolved in 7 mL of methanol. 0.4 mL of 0.34 M solution of LaCl$_3$*7H$_2$O (0.136 mmol) in methanol was added, followed by 0.4 mL (0.726 g/mL, 2.88 mmol) of triethylamine. The mixture was heated under reflux for 4 hours, after that evaporated to dryness. 2-Propanol (7 mL) was added and the suspension was heated under reflux for 10 minutes and then filtered (quite slow filtration, very fine precipitate). The solid on filter was washed with 2-propanol and dried in oven at 100° C. for 10 min. Yield 56 mg. (86%)

VNK-517

VNK-514 (130 mg, 0.16 mmol) was dissolved in 10 ml of methanol. 0.4 mL of 0.38 M solution of TbCl$_3$*6H$_2$O (0.18 mmol) in methanol was added, followed by 0.22 mL (0.726 g/mL, 1.6 mmol) of TEA. The mixture was heated under reflux for 24 hours, after that evaporated to dryness to give the final complex.

VNK-609

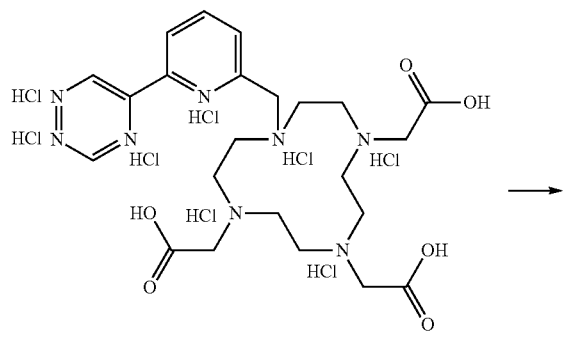

Molecular Weight: 808.22

VNK-514

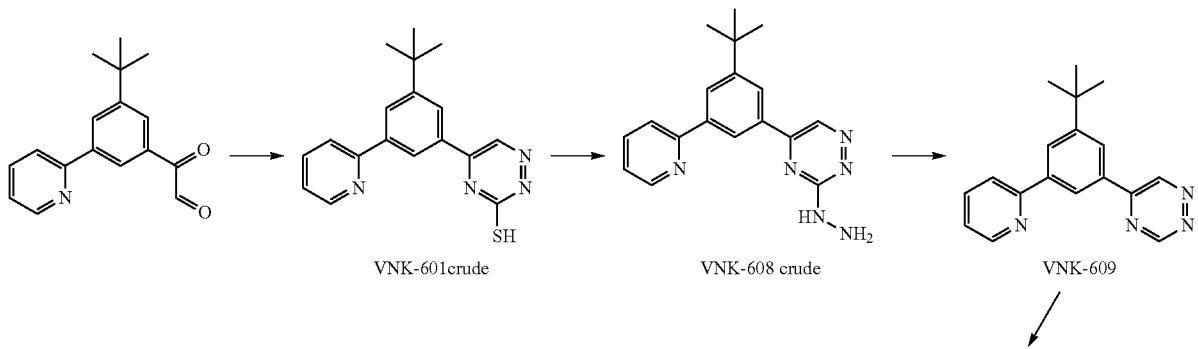

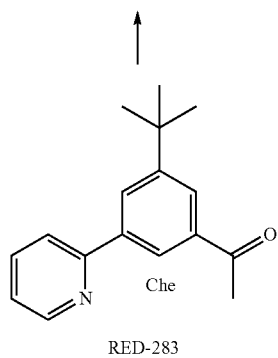

RED-283

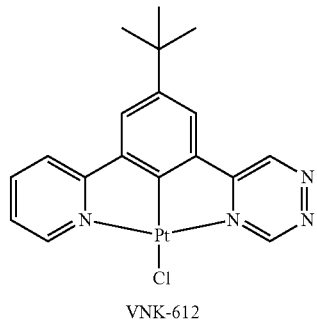

VNK-612

RED-283 (1.675 g, 6.6 mmol) was dissolved in dioxane (25 mL). Selenium dioxide (0.735 g, 6.6 mmol) was dissolved in a mixture of dioxane (5 ml) and water (0.2 mL) at heating. The SeO₂ solution was added to the solution of RED-283 and the mixture was heated under reflux for 24 hours. The mixture was filtered while boiling hot. The filtrate was evaporated to dryness to give yellow oil. This product was used in the next step without any further purification.

The crude product from previous step was dissolved in ethanol (10 mL). Thiosemicarbazide (590 mg, 6.6 mmol) was added, followed by water (15 mL) and K₂CO₃ (1.38 g, 10 mmol, 1.3 eq). The mixture was stirred at RT for 5 minutes. Ethanol was evaporated by rotary evaporation (bath temperature 94° C.). The aqueous solution was stirred for 15 minutes at 94° C., then allowed to cool to RT. The mixture was transferred into a beaker (250 mL) and acetic acid (6 mL) was added causing formation of a solid. The solid was filtered off, washed with water to give VNK-601. This product was used in the next step without any further purification.

A mixture of crude mercaptotriazine VNK-601 from previous step, ethanol (25 mL) and hydrazine (0.63 mL, approx. 3 eq) was heated under reflux for 14 hours. Water was added and the mixture was extracted with DCM. Organic layer was dried over MgSO₄, filtered and evaporated to dryness to give VNK-608 crude. This product was used in the next step without any further purification.

A mixture of VNK-608 crude, methanol (100 mL) and sodium methoxide (2.48 g, 50 mmol) was stirred at 75° C. (bath temperature) for 14 hours. Acetic acid (5 mL) was added and the mixture was evaporated to a volume of approximately 5 mL. Water and conc. ammonia (2 mL) were added causing formation of an oily precipitate. Water was decanted. The residue was dried on rotary evaporator under vacuum at 90° C. The product VNK-609 was purified by using Isolera machine (25 g cartridge and a mixture of DCM (70%) and EA (30%)). Yield 270 mg (14% overall after 4 steps). ¹H NMR (400 MHz, DMSO-D₆): δ 9.81 (d, J=2.4 Hz, 1H), 9.69 (d, J=2.4 Hz, 1H), 8.75 (m, 1H), 8.59 (t, J=1.6 Hz, 1H), 8.28 (m, 1H), 7.82 (m, 1H), 7.31 (m, 1H), 1.44 (s, 9H).

VNK-612

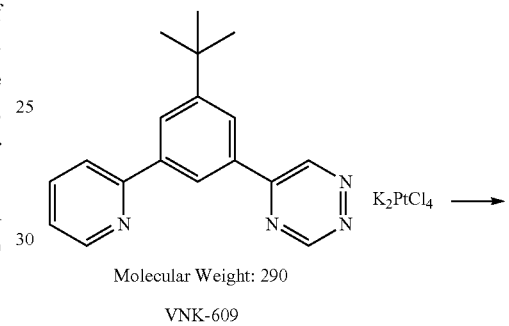

Molecular Weight: 290

VNK-609

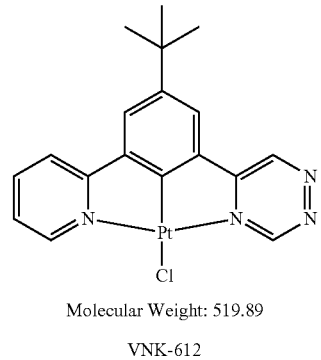

Molecular Weight: 519.89

VNK-612

The starting ligand VNK-609 (170 mg, 0.586 mmol) was dissolved in acetic acid (25 mL). To this solution, potassium tetrachloroplatinate (240 mg, 0.58 mmol) was added and the mixture was heated under reflux under argon atmosphere for 18 hours. The mixture was allowed to cool to RT and filtered. The dark solid on the filter was washed with methanol, water and again methanol. (234 mg). NMR showed mixture of products. The solid was placed into a test tube, 4 mL of DMSO was added and the mixture was heated until boiling begins. After that the mixture was allowed to cool to RT, methanol (8 mL) was added and the mixture was filtered to give red solid on filter. Yield 75 mg (25%).

VNK-614

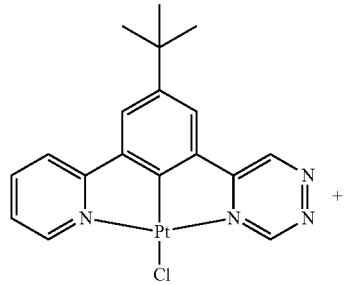

Molecular Weight: 519.89

VNK-612

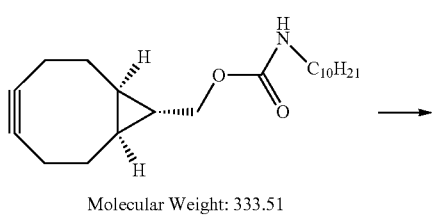

Molecular Weight: 333.51

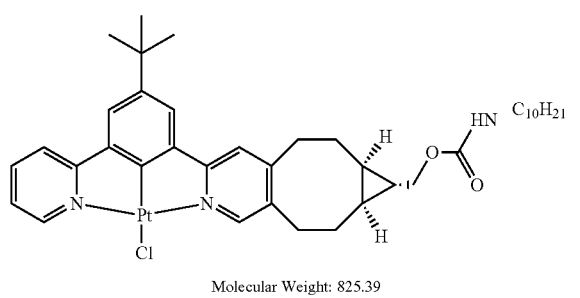

Molecular Weight: 825.39

VNK-614

In an NMR tube VNK-612 (35 mg, 0.067 mmol) was suspended in DMSO-$D_6$ (0.6 mL). BCN-C10 (27 mg, 0.08 mmol, 1.2 eq) was added. The mixture was heated to boiling point. Evaluation of nitrogen was apparent. NMR showed 100% conversion to the product. $^1$H NMR (400 MHz, DMSO-$D_6$): δ 9.35 (d, J=5.2 Hz Pt satellites, 1H), 8.91 (s, Pt satellites, 1H), 7.92 (br.t, J=7.2 Hz, 1H), 7.70 9br.d, J=7.2 Hz, 1H), 7.47 (s, 2H), 7.41 (s, Pr satellites, 1H), 7.25 (m, 1H), 4.6 (br.s, 1H), 3.82 (m, 2H), 2.5-3.2 (m, 8H), 1.27 (m, 16H), 0.8 (m, 12H).

VNK-450

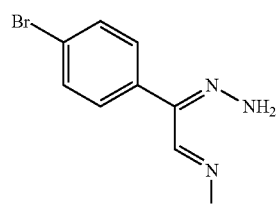

Molecular Weight: 242.07

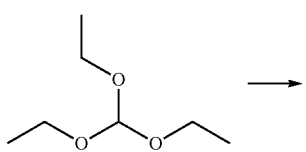

Molecular Weight: 148.20
d = 0.891 g/mL

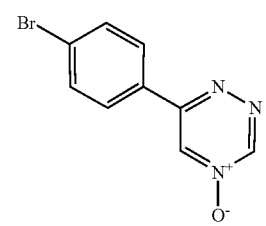

Molecular Weight: 252.07

A mixture of the hydrazine (24.2 g, 100 mmol) and triethylorthoformyate (18 mL, 16 g, 108 mmol) was heated until all the starting material dissolved. Catalytic amount of para toluene sulphonic acid was added and the mixture was heated under reflux for 1 hour (during this time quite a lot of precipitate formed). The mixture was allowed to cool to RT and the solid was filtered off, washed with methanol and dried. Yield 13 g (52%).

VNK-457

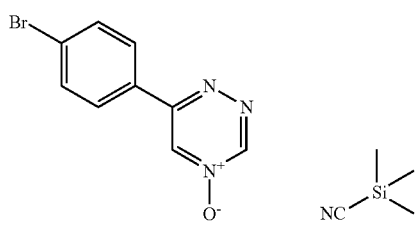

Molecular Weight: 252.07          Molecular Weight: 99.21

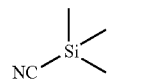

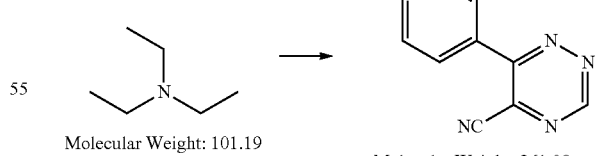

Molecular Weight: 101.19

Molecular Weight: 261.08

1,2,4-triazine-4-oxide (5.04 g, 20 mmol) was suspended in DCM (40 mL). Trimethylsilyl cyanide (2.4 g, 24 mmol, 1.2 eq) was added, followed by trimethylamine (2.4 g, 24 mmol). The mixture was heated under reflux for 15 minutes and then filtered through a pad of silica gel collecting yellow fraction. The solvent was evaporated to give a pure product. Yield 2.2 g (42%).

VNK-458

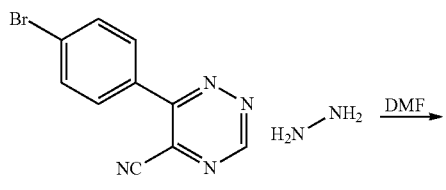

Molecular Weight: 261.08

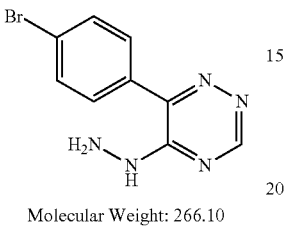

Molecular Weight: 266.10

5-cyano-1,2,4-triazine (2.1 g, 8 mmol) was dissolved in DMF (10 mL). To this solution, hydrazine hydrate (1.33 g, 26.6, 3.3 eq) was added. The mixture was stirred at RT for 15 minutes then at 60-70° C. for 10 minutes. The mixture was allowed to cool to RT and water 50 mL was added. Precipitated solid was filtered off, washed with water and dried to give VNK-458 as yellow solid. Yield 2.0 g (94%).

VNK-459

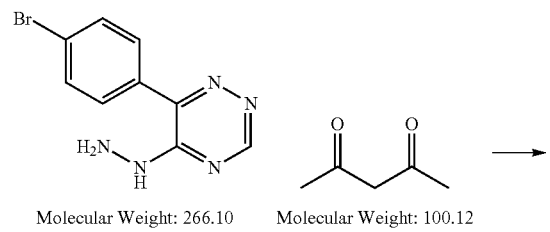

Molecular Weight: 266.10   Molecular Weight: 100.12

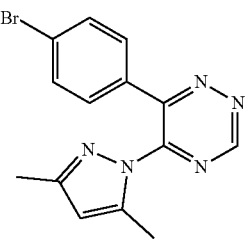

Molecular Weight: 330.18

To a stirred suspension 3-hydrazino-1,2,4-triazine (517 mg, 1.94 mmol) in ethanol (15 mL) acetylacetone (213 mg, 2.13 mmol) was added. The mixture was heated under reflux for 30 minutes. The mixture was allowed to cool to RT and the solid was filtered off, washed with ethanol to give VNK-459. Yield 527 mg (82%).

VNK-461

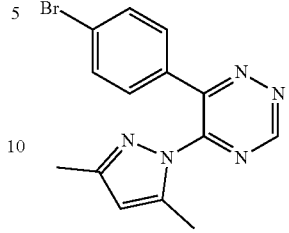

Molecular Weight: 330.18
VNK-459

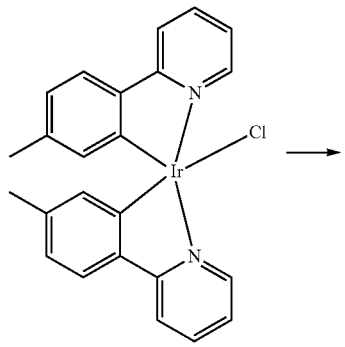

Molecular Weight: 564.10
VNK-411

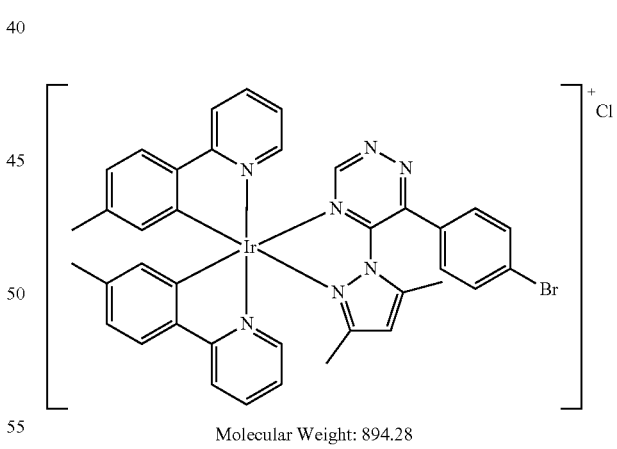

Molecular Weight: 894.28

VNK-421 Chloride

A mixture of [Ir(tpy)2]Cl2 VNK-411 (226 mg, 0.4 mmol for Ir), VNK-459 (145 mg, 0.44 mmol, 1.1 eq), chloroform (10 mL) and methanol (10 mL) was heated under reflux for 2 hours. The solvent was evaporated to a volume of approximately 2 mL. Diethyl ether (10 mL) was added. Precipitated solid was filtered off, washed with ether to give VNK-461 (230 mg). (64%)

VNK-234

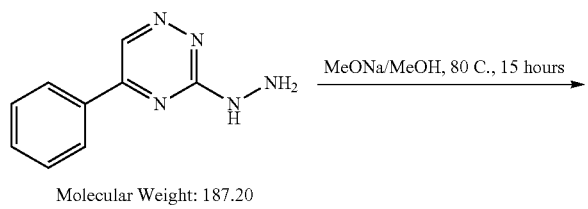

Molecular Weight: 187.20

VNK-194

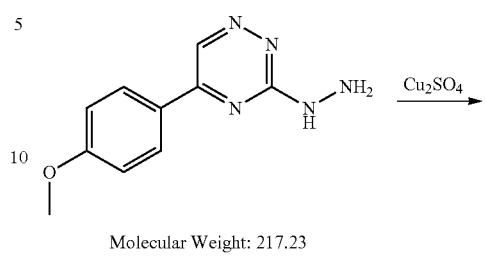

Molecular Weight: 217.23

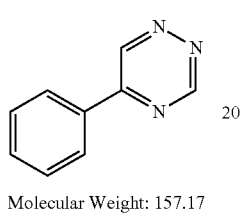

Molecular Weight: 157.17

Sodium (600 mg, 26 mmol, 6 eq.) was dissolved in methanol (50 mL). To this solution, 3-hydrazino-1,2,4-triazine (800 mg, 4.27 mmol) was added (dark solution formed immediately) and the mixture has stirred at 80° C. for 15 hours. Excess of acetic acid (5-8 mL) was added and the mixture was evaporated. Water (50 mL) was added followed by a little amount of ammonia solution (to neutralise remaining AcOH). Precipitated solid was filtered off, washed with water to give the crude product. After drying the solid was purified by column chromatography (silica gel, ethylacetate). Yield 330 mg (49%).

VNK-472

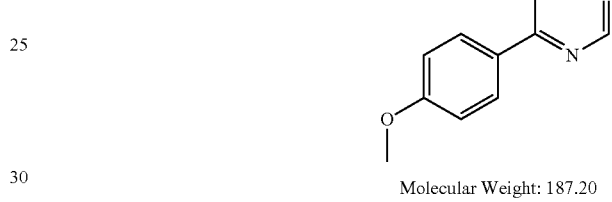

A mixture of the hydrazine triazine (2 g, 10.4 mmol), methanol (100 mL) and sodium methoxide (5.9 g, 109 mmol) was stirred at 75° C. (bath temperature) for 14 hours. Acetic acid (5 mL) and water (20 mL) were added and the mixture was evaporated to a volume of approximately 15 mL. The mixture was basified by addition of 33% aqueous ammonia (5 mL). Precipitated solid was filtered off, washed with water (20 mL) and dried. The product was then purified by column chromatography.

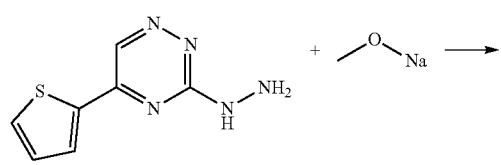

Molecular Weight: 187.20

3-Hydrazino-5-(4-methoxyphenyl)-1,2,4-triazine (8.8 g, 40 mmol) was dissolved in acetic acid (220 mL) at slight heating, the mixture was allowed to cool to RT. $Cu_2SO_4$ (17.6 g) and NaOAc (17.6 g) were dissolved in water (220 mL) and this solution was added to the first one. The mixture was stirred at RT for 14 hours and then evaporated to dryness by rotary evaporation under reduced pressure. The residue was triturated with ethyl acetate (100 ml) and DCM (100 mL) and filtered. The solid on filter was washed with DCM and discarded. The filtrate was evaporated to dryness, dissolved in DCM and filtered through short pad of silica gel. The solvent was removed to give the pure product.

VNK-469

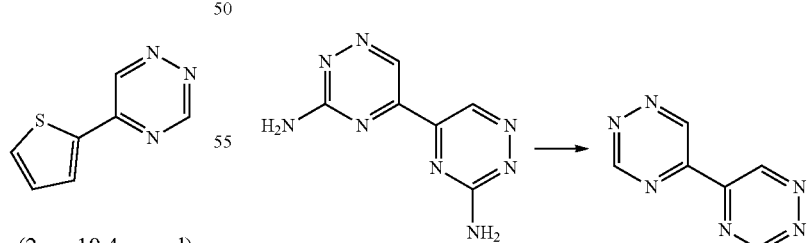

Molecular Weight: 190.17

The diamino derivative (750 mg) was suspended in DMF (20 mL). Butyl nitrite (4 mL) was added and the mixture was heated under reflux for 14 hours. All volatiles were removed by rotary evaporation. The product was purified by column chromatography. Yield 5%.

Kinetics

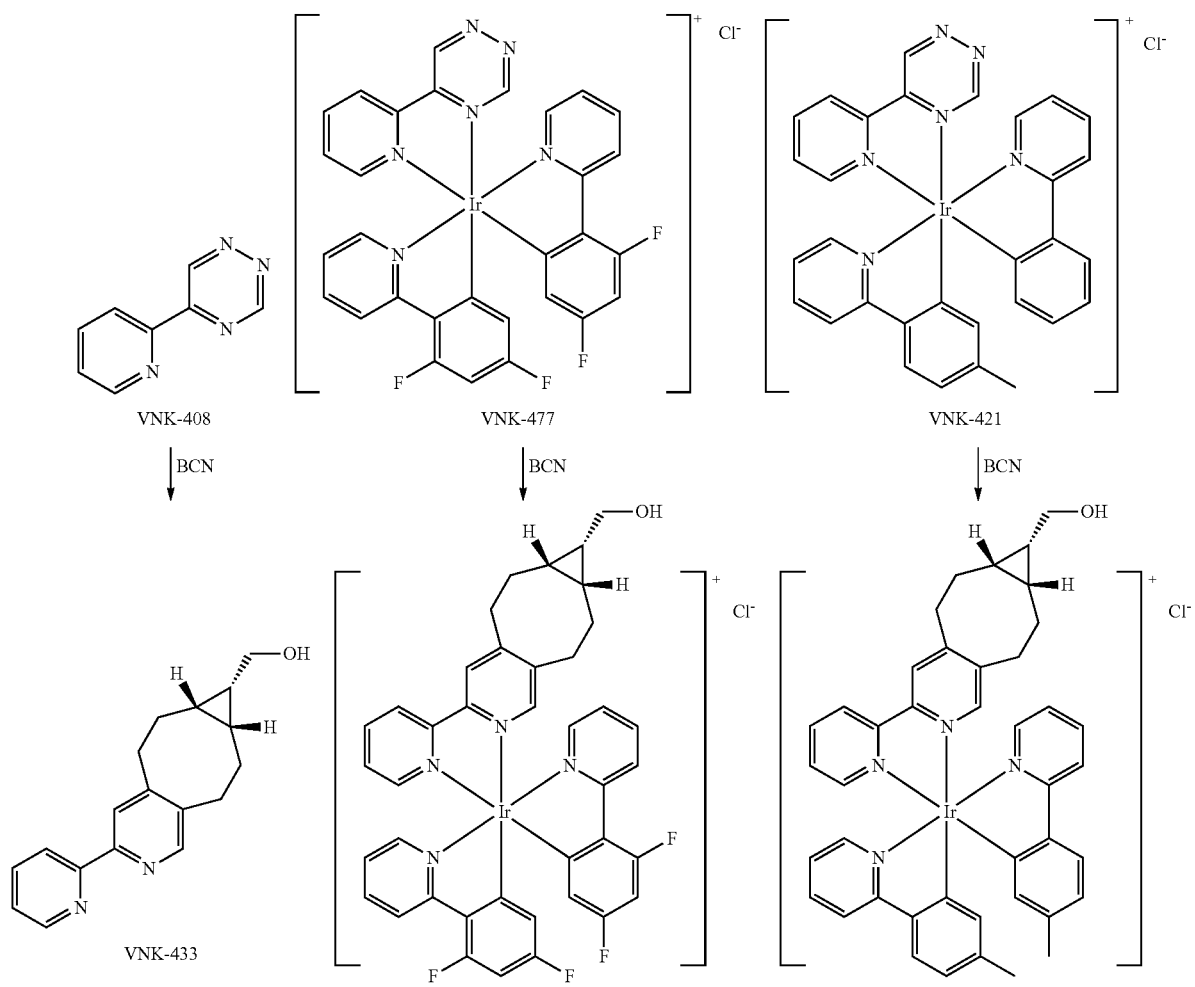

IEDDA Reaction Kinetics

The reaction between the tetrazine and triazine iridium complexes (the substrates) and the alkyne BCN were carried out in methanol at 25° C. under pseudo-first order conditions, with BCN in at least 10-fold excess. Reactions were followed by monitoring the loss of the substrate absorbance spectrophotometrically at a suitable wavelength. Observed pseudo-first-order rate constants, $k_{obs}$, were obtained using nonlinear regression of the monoexponential loss of absorbance with time. Second order rate constants, $k_2$, were obtained from linear regression of plots of $k_{obs}$ against BCN concentration. Pseudo-first-order and second order plots are shown below. The data is summarised in Table 1.

The alkyne BCN has the following structure

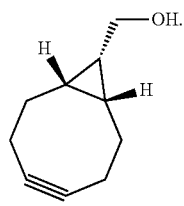 [SMILES: OC[C@H]1[C@H]2CCC#CCC[C@@H]12]

TABLE 1

Second order rate constants, $k_2$, for the reaction between triazine iridium complexes and BCN. Except where stated, reactions were carried out spectrophotometrically in methanol at 25° C.

| Compound | $k_2 / M^{-1} s^{-1}$ |
|---|---|
| VNK408 | 0.059 ± 0.001 |
| VNK477 (Cl⁻ salt) | 7.87 ± 0.32 |
| VNK477 (PF₆⁻ salt) | 8.23 ± 0.31 |
| VNK421 (Cl⁻ salt) | 7.745 ± 0.131 |

This data demonstrates that N4-complexation of the triazine to Ir(III) centre increases the rate constant by more than two orders of magnitude.

The invention claimed is:

1. A method of forming a pyridine; the method comprising:
   contacting a compound comprising a 1,2,4-triazine with a compound comprising a dienophile to form a compound comprising a pyridine,
   wherein the 1,2,4-triazine is complexed to a metal.

2. A method of claim 1, wherein the compound comprising the 1,2,4-triazine is a compound of formula (I):

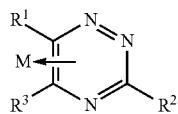

wherein M is the metal, which may be bonded to other ligands;

$R^1$, $R^2$ and $R^3$ are each independently selected from H, $C_1$-$C_6$-alkyl, $C_1$-$C_6$-haloalkyl, $C_3$-$C_6$ alkenyl, $C_1$-$C_6$-alkynyl, halo, nitro, cyano, $C(O)R_4$, $(CH_2)_nCO_2R^4$, $OR^4$, $SR^4$, $NR^4R^5$, $C(O)NR^4R^4$, $S(O)R^4$, $S(O)_2R^4$, $C_3$-$C_6$-cycloalkyl, 3-18-membered heterocycloalkyl, 5-, 6-, 9-, 10- or 14-membered heteroaryl, phenyl, naphthyl, pyrenyl and fluorophore; or $R^1$ and $R^3$, together with the atom to which they are attached, form a monocyclic or polycyclic aryl or heteroaryl;

wherein if any of $R^1$, $R^2$ and $R^3$ are $C_1$-$C_6$-alkyl, $C_3$-$C_6$-cycloalkyl, 3-6-membered heterocycloalkyl, 5-, 6-, 9-, 10- or 14-membered heteroaryl, phenyl, naphthyl or pyrenyl, that group can be substituted with from 1 to 5 $R^6$ groups;

$R^4$ is independently at each occurrence selected from H and $C_1$-$C_4$-alkyl; and $R^5$ is independently at each occurrence selected from H, $C_1$-$C_4$-alkyl, $C(O)$—$C_1$-$C_4$-alkyl and $S(O)_2$—$C_1$-$C_4$-alkyl;

$R^6$ is selected from 3-18-membered heterocycloalkyl, 5-, 6-, 9-,10- or 14-membered heteroaryl, fluorophore, phenyl, naphthyl, $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $N((CH_2)_nCO_2R_4)_2$, $C(O)NR^4R^4$, $S(O)R^4$ and $S(O)_2R^4$;

wherein if $R^6$ is 3-18-membered heterocycloalkyl, $C_1$-$C_6$-alkyl, 5-, 6-, 9-,10- or 14-membered heteroaryl, phenyl, or naphthyl, $R^6$ can be substituted with from 1 to 5 $R^7$ groups;

$R^7$ is selected from 3-18-membered heterocycloalkyl, 5-, 6-, 9-,10- or 14-membered heteroaryl, fluorophore, phenyl, naphthyl, $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $N((CH_2)_nCO_2R_4)_2$, $C(O)NR^4R^4$, $S(O)R^4$ and $S(O)_2R^4$;

wherein if $R^7$ is 3-18-membered heterocycloalkyl, $C_1$-$C_6$-alkyl, 5-, 6-, 9-,10- or 14-membered heteroaryl, phenyl, or naphthyl then $R^7$ can be substituted with from 1 to 5 $R^8$ groups;

$R^8$ is selected from $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $C(O)NR^4R^4$, $S(O)R^4$ and $S(O)_2R^4$;

wherein the compound of formula (I) optionally comprises a biological targeting moiety that is attached via one of the alkyl, $C_3$-$C_6$-alkenyl, $C_1$-$C_6$-alkynyl, $C_3$-$C_6$-cycloalkyl, 3-6-membered heterocycloalkyl, 5-, 6-, 9-,10- or 14-membered heteroaryl, phenyl, naphthyl groups of $R^1$, $R^2$, $R^3$, $R^4$, $R^5$, $R^6$, $R^7$ or $R^8$;

n is independently at each occurrence an integer selected from 0, 1 and 2;

where any of $R^6$, $R^7$ or $R^8$ are phenyl, said phenyl group may be bonded to the metal;

where any of $R^2$, $R^3$, $R^6$, $R^7$ or $R^8$ are $SR^4$, $NR^4R^5$, $(CH_2)_nCOOR^4$, $OR^4$ or $N((CH_2)_nCO_2R_4)_2$, $R^4$ may be absent and the S, N or O may be bonded to the metal.

3. A method of claim 2, wherein $R^3$ is a 5-, 6-, 9-, 10- or 14-membered heteroaryl group.

4. A method of claim 2, wherein $R^3$ is a 2-pyridyl group.

5. A method of claim 2, wherein $R^2$ is H.

6. A method of claim 2, wherein $R^1$ is H.

7. The method of claim 2, wherein $R^1$, $R^2$, $R^3$, $R^6$ and $R^7$ are selected such that the compound comprising the 1,2,4-triazine further comprises a fluorophore.

8. The method of claim 1, wherein the dienophile is a $C_3$-$C_{10}$-cycloalkene or $C_7$-$C_{10}$-cycloalkyne.

9. The method of claim 1, wherein the metal is a transition metal, actinide or lanthanide.

10. The method of claim 1, wherein the metal is selected from Ru, Ir, Eu, Gd, Tb, Pt, Re, Tc, and Zn.

11. The method of claim 1, wherein the metal is complexed to one or more ligands other than the 1,2,4-triazine.

12. The method of claim 1, wherein the compound comprising the 1,2,4-triazine further comprises a biological targeting moiety.

13. The method of claim 12, wherein the method is a method of medical imaging or imaging a biological sample and wherein the compound comprising the 1,2,4-triazine further comprises a biological targeting moiety and the method comprises:
administering the compound comprising the 1,2,4-triazine to a subject or a biological sample; and
administering the compound comprising the dienophile to the subject or a biological sample, in order to contact the compound comprising the dienophile with the compound comprising the 1,2,4-triazine to form the compound comprising the pyridine; and
detecting the image.

14. The method of claim 1, wherein the compound comprising the dienophile further comprises a biological targeting moiety.

15. The method of claim 14, wherein the method is a method of medical imaging or imaging a biological sample and wherein the compound comprising the dienophile further comprises a biological targeting moiety and the method comprises:
administering the compound comprising the dienophile to a subject or a biological sample; and
administering the compound comprising the 1,2,4-triazine to the subject or a biological sample, in order to contact the compound comprising the 1,2,4-triazine with the compound comprising the dienophile to form the compound comprising the pyridine; and
detecting the image.

16. A kit for medical imaging or for imaging a biological sample, the kit comprising:
a compound comprising a 1,2,4-triazine; and
a compound comprising a dienophile;
wherein the 1,2,4-triazine is complexed to a metal; and
wherein either:
A) the compound comprising the 1,2,4-triazine further comprises a biological targeting moiety; or
B) the compound comprising the dienophile further comprises a biological targeting moiety.

17. The kit of claim 16, wherein the compound comprising the 1,2,4-triazine is a compound of formula (I):

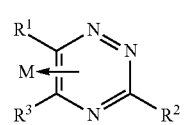

wherein M is the metal, which may be bonded to other ligands;

$R^1$, $R^2$ and $R^3$ are each independently selected from H, $C_1$-$C_6$-alkyl, $C_1$-$C_6$-haloalkyl, $C_3$-$C_6$ alkenyl, $C_1$-$C_6$-alkynyl, halo, nitro, cyano, $C(O)R_4$, $(CH_2)_nCO_2R^4$, $OR^4$, $SR^4$, $NR^4R^5$, $C(O)NR^4R^4$, $S(O)R^4$, $S(O)_2R^4$, $C_3$-$C_6$-cycloalkyl, 3-18-membered heterocycloalkyl, 5-, 6-, 9-,10 or 14-membered heteroaryl, phenyl, naphthyl, pyrenyl and fluorophore; or $R^1$ and $R^3$, together with the atom to which they are attached, form a monocyclic or polycyclic aryl or heteroaryl;

wherein if any of $R^1$, $R^2$ and $R^3$ are $C_1$-$C_6$-alkyl, $C_3$-$C_6$-cycloalkyl, 3-6-membered heterocycloalkyl, 5-, 6-, 9-, 10- or 14-membered heteroaryl, phenyl, naphthyl or pyrenyl that group can be substituted with from 1 to 5 $R^6$ groups;

$R^4$ is independently at each occurrence selected from H and $C_1$-$C_4$-alkyl; and $R^5$ is independently at each occurrence selected from H, $C_1$-$C_4$-alkyl, C(O)—$C_1$-$C_4$-alkyl and $S(O)_2$—$C_1$-$C_4$-alkyl;

$R^6$ is selected from 3-18-membered heterocycloalkyl, 5-, 6-, 9-,10- or 14-membered heteroaryl, fluorophore, phenyl, naphthyl, $C_1$-$C_6$-alkyl, $C_1$-$C_6$-haloalkyl, $C_3$-$C_6$-alkenyl, $C_1$-$C_6$-alkynyl, halo, nitro, cyano, C(O)$R^4$, $(CH_2)_nCO_2R^4$, $OR^4$, $SR^4$, $NR^4R^5$, $N((CH_2)_nCO_2R_4)_2$, $C(O)NR^4R^4$, $S(O)R^4$ and $S(O)_2R^4$;

wherein if $R^6$ is 3-18-membered heterocycloalkyl, $C_1$-$C_6$-alkyl, 5-, 6-, 9-,10- or 14-membered heteroaryl, phenyl, or naphthyl, $R^6$ can be substituted with from 1 to 5 $R^7$ groups;

$R^7$ is selected from 3-18-membered heterocycloalkyl, 5-, 6-, 9-,10- or 14-membered heteroaryl, fluorophore, phenyl, naphthyl, $C_1$-$C_6$-alkyl, $C_1$-$C_6$-haloalkyl, $C_3$-$C_6$-alkenyl, $C_1$-$C_6$-alkynyl, halo, nitro, cyano, C(O)$R^4$, $(CH_2)_nCO_2R^4$, $OR^4$, $SR^4$, $NR^4R^5$, $N((CH_2)_nCO_2R_4)_2$, $C(O)NR^4R^4$, $S(O)R^4$ and $S(O)_2R^4$;

wherein if $R^7$ is 3-18-membered heterocycloalkyl, $C_1$-$C_6$-alkyl, 5-, 6-, 9-,10- or 14-membered heteroaryl, phenyl, or naphthyl then $R^7$ can be substituted with from 1 to 5 $R^8$ groups;

$R^8$ is selected from $C_1$-$C_6$-alkyl, $C_1$-$C_6$-haloalkyl, $C_3$-$C_6$-alkenyl, $C_1$-$C_6$-alkynyl, halo, nitro, cyano, $C(O)R^4$, $(CH_2)_nCO_2R^4$, $OR^4$, $SR^4$, $NR^4R^5$, $C(O)NR^4R^4$, $S(O)R^4$ and $S(O)_2R^4$;

wherein the compound of formula (I) optionally comprises a biological targeting moiety that is attached via one of the alkyl, $C_3$-$C_6$-alkenyl, $C_1$-$C_6$-alkynyl, $C_3$-$C_6$-cycloalkyl, 3-6-membered heterocycloalkyl, 5-, 6-, 9-, 10- or 14-membered heteroaryl, phenyl, naphthyl groups of $R^1$, $R^2$, $R^3$, $R^4$, $R^5$, $R^6$, $R^7$ or $R^8$;

n is independently at each occurrence an integer selected from 0, 1 and 2;

where any of $R^6$, $R^7$ or $R^8$ are phenyl, said phenyl group may be bonded to the metal;

where any of $R^2$, $R^3$, $R^6$, $R^7$ or $R^8$ are $SR^4$, $NR^4R^5$, $(CH_2)_nCOOR^4$, $OR^4$ or $N((CH_2)_nCO_2R_4)_2$, $R^4$ may be absent and the S, N or O may be bonded to the metal.

18. A kit of claim 17, wherein $R^3$ is a 5-, 6-, 9-, 10- or 14-membered heteroaryl group.

19. A kit of claim 17, wherein $R^3$ is a 2-pyridyl group.

20. A kit of claim 17, wherein $R^2$ is H.

21. A kit of claim 17, wherein $R^1$ is H.

22. A kit of claim 17, wherein $R^1$, $R^2$, $R^3$, $R^6$ and $R^7$ are selected such that the compound comprising the 1,2,4-triazine further comprises a fluorophore.

23. A kit of claim 16, wherein the dienophile is a $C_3$-$C_{10}$-cycloalkene or $C_5$-$C_{10}$-cycloalkyne.

24. A kit of claim 16, wherein the metal is a transition metal, actinide or lanthanide.

25. A kit of claim 16, wherein the metal is selected from Ru, Ir, Eu, Gd, Tb, Pt, Re, Tc, and Zn.

26. A kit of claim 16, wherein the metal is complexed to one or more ligands other than the 1,2,4-triazine.

27. A kit of claim 16 wherein the compound comprising the 1,2,4-triazine further comprises a biological targeting moiety.

28. A kit of claim 16, wherein the compound comprising the dienophile further comprises a biological targeting moiety.

* * * * *